12) United States Patent
Chi Sing et al.

(10) Patent No.: US 9,067,063 B2
(45) Date of Patent: Jun. 30, 2015

(54) EXPANDABLE BRACHYTHERAPY APPARATUS AND METHODS FOR USING THEM

(75) Inventors: Eduardo Chi Sing, Dana Point, CA (US); Tommy G. Nguyen, Irvine, CA (US)

(73) Assignee: CIANNA MEDICAL, INC., Aliso Viejo, CA (US)

(*) Notice: Subject to any disclaimer, the term of this patent is extended or adjusted under 35 U.S.C. 154(b) by 472 days.

(21) Appl. No.: 12/939,121

(22) Filed: Nov. 3, 2010

(65) Prior Publication Data

US 2012/0108881 A1 May 3, 2012

(51) Int. Cl.
*A61M 36/04* (2006.01)
*A61M 36/12* (2006.01)
*A61N 5/10* (2006.01)
*A61M 25/10* (2013.01)

(52) U.S. Cl.
CPC ............ *A61N 5/1015* (2013.01); *A61N 5/1001* (2013.01); *A61M 25/10* (2013.01); *A61N 5/1014* (2013.01); *A61N 5/1007* (2013.01); *A61N 5/1002* (2013.01); *A61N 2005/1004* (2013.01)

(58) Field of Classification Search
CPC . A61N 5/1001; A61N 5/1002; A61N 5/1007; A61N 5/1014; A61N 5/1027; A61N 2005/1002; A61N 2005/1003; A61N 2005/1004; A61M 25/10
USPC ..................................... 600/3, 7, 8
See application file for complete search history.

(56) References Cited

U.S. PATENT DOCUMENTS 3,060,924 A 10/1962 Rush
3,750,653 A 8/1973 Simon
3,968,803 A 7/1976 Hyman
4,427,005 A 1/1984 Tener
4,580,561 A 4/1986 Williamson
4,706,652 A 11/1987 Horowitz
4,714,074 A 12/1987 Rey et al.
4,798,212 A 1/1989 Arana
4,936,823 A 6/1990 Colvin et al.
4,957,476 A 9/1990 Cano
4,976,680 A 12/1990 Hayman et al.
5,056,523 A 10/1991 Hotchkiss, Jr. et al.
5,106,360 A 4/1992 Ishiwara et al.
5,152,741 A 10/1992 Farnio
5,235,966 A 8/1993 Jamner
5,242,372 A 9/1993 Carol
5,279,565 A 1/1994 Klein et al.
5,302,168 A 4/1994 Hess
5,336,178 A 8/1994 Kaplan et al.
5,354,257 A 10/1994 Roubin et al.

(Continued)

*Primary Examiner* — Charles A Marmor, II
*Assistant Examiner* — Thaddeus Cox
(74) *Attorney, Agent, or Firm* — William A. English; Vista IP Law Group LLP

(57) ABSTRACT

Brachytherapy treatment apparatus are provided that include an elongate core member, a plurality of expandable catheters or other elongate members and a balloon or other expandable member on a distal portion adjacent the core member. Each catheter includes a distal end coupled to the core member distal end, a proximal end movable relative to the core member, and a lumen extending between the proximal and distal ends for receiving a source of radiation therealong. The balloon is expandable independently of the catheters such that the balloon may be expanded after expanding the catheters, e.g., to facilitate imaging and/or dose planning. Optionally, a working channel may be provided for receiving an aspiration catheter or other instrument or at least one of the catheters may include an aspiration lumen and one or more ports, e.g., for aspirating material from a region surrounding the distal portion.

27 Claims, 15 Drawing Sheets

(56) References Cited

U.S. PATENT DOCUMENTS

| | | |
|---|---|---|
| 5,411,466 A | 5/1995 | Hess |
| 5,423,747 A | 6/1995 | Amano |
| 5,429,582 A | 7/1995 | Williams |
| 5,429,605 A | 7/1995 | Richling et al. |
| 5,484,384 A | 1/1996 | Fearnot |
| 5,503,613 A | 4/1996 | Weinberger |
| 5,509,900 A | 4/1996 | Kirkman |
| 5,538,502 A | 7/1996 | Johnstone |
| 5,540,659 A | 7/1996 | Teirstein |
| 5,611,767 A | 3/1997 | Williams |
| 5,653,683 A | 8/1997 | D'Andrea |
| 5,678,572 A | 10/1997 | Shaw et al. |
| 5,707,332 A | 1/1998 | Weinberger |
| 5,713,828 A | 2/1998 | Coniglione |
| 5,720,717 A | 2/1998 | D'Andrea |
| 5,730,698 A | 3/1998 | Fischell et al. |
| 5,752,970 A * | 5/1998 | Yoon ............................ 606/185 |
| 5,782,740 A | 7/1998 | Schneiderman |
| 5,840,008 A | 11/1998 | Klein et al. |
| 5,843,163 A | 12/1998 | Wall |
| 5,851,171 A | 12/1998 | Gasson |
| 5,863,284 A | 1/1999 | Klein |
| 5,882,291 A | 3/1999 | Bradshaw et al. |
| 5,891,091 A | 4/1999 | Teirstein |
| 5,910,102 A | 6/1999 | Hastings |
| 5,913,813 A | 6/1999 | Williams et al. |
| 5,916,143 A | 6/1999 | Apple et al. |
| 5,931,774 A | 8/1999 | Williams et al. |
| 5,938,582 A | 8/1999 | Ciamacco, Jr. et al. |
| 5,942,209 A | 8/1999 | Leavitt et al. |
| 5,976,106 A | 11/1999 | Verin et al. |
| 6,013,019 A | 1/2000 | Fischell et al. |
| 6,022,308 A | 2/2000 | Williams |
| 6,030,333 A | 2/2000 | Sioshansi et al. |
| 6,033,357 A | 3/2000 | Ciezki et al. |
| 6,036,632 A | 3/2000 | Whitmore et al. |
| 6,056,722 A | 5/2000 | Jayaraman |
| 6,059,752 A | 5/2000 | Segal |
| 6,071,263 A | 6/2000 | Kirkman |
| 6,074,339 A | 6/2000 | Ganbale et al. |
| 6,083,148 A | 7/2000 | Williams |
| 6,117,064 A | 9/2000 | Apple et al. |
| 6,159,139 A | 12/2000 | Chiu |
| 6,159,141 A | 12/2000 | Apple et al. |
| 6,176,821 B1 | 1/2001 | Crocker et al. |
| 6,179,766 B1 | 1/2001 | Dickerson |
| 6,196,996 B1 | 3/2001 | Teirstein |
| 6,200,256 B1 | 3/2001 | Weinberger |
| 6,200,257 B1 | 3/2001 | Winkler |
| 6,213,976 B1 | 4/2001 | Trerotola |
| 6,217,585 B1 | 4/2001 | Houser et al. |
| 6,221,003 B1 | 4/2001 | Sierocuk et al. |
| 6,221,030 B1 | 4/2001 | Avaltroni |
| 6,234,951 B1 | 5/2001 | Hastings |
| 6,238,374 B1 | 5/2001 | Winkler |
| 6,258,099 B1 | 7/2001 | Mareiro et al. |
| 6,261,320 B1 | 7/2001 | Tam et al. |
| 6,264,599 B1 | 7/2001 | Slater et al. |
| 6,264,631 B1 | 7/2001 | Willis et al. |
| 6,267,775 B1 | 7/2001 | Clerc et al. |
| 6,287,249 B1 | 9/2001 | Tam et al. |
| 6,338,709 B1 | 1/2002 | Geoffrion |
| 6,358,195 B1 | 3/2002 | Green et al. |
| 6,371,904 B1 | 4/2002 | Sirimanne et al. |
| 6,413,204 B1 | 7/2002 | Winkler et al. |
| 6,458,069 B1 | 10/2002 | Tam et al. |
| 6,482,142 B1 | 11/2002 | Winkler et al. |
| 6,482,178 B1 | 11/2002 | Andrews et al. |
| 6,494,824 B1 | 12/2002 | Apple et al. |
| 6,506,145 B1 | 1/2003 | Bradshaw et al. |
| 6,508,784 B1 | 1/2003 | Shu |
| 6,527,692 B1 | 3/2003 | Weinberger |
| 6,527,693 B2 | 3/2003 | Munro, III et al. |
| 6,537,194 B1 | 3/2003 | Winkler |
| 6,540,656 B2 | 4/2003 | Fontayne et al. |
| 6,540,734 B1 | 4/2003 | Chiu et al. |
| 6,554,757 B1 | 4/2003 | Geitz |
| 6,582,353 B1 | 6/2003 | Hastings et al. |
| 6,589,158 B2 | 7/2003 | Winkler |
| 6,592,548 B2 | 7/2003 | Jayaraman |
| 6,607,476 B1 | 8/2003 | Barnhart |
| 6,607,478 B2 | 8/2003 | Williams |
| 6,638,206 B2 | 10/2003 | Green et al. |
| 6,641,518 B2 | 11/2003 | Wolfson et al. |
| 6,645,135 B1 | 11/2003 | Bhat |
| 6,648,811 B2 | 11/2003 | Sierocuk et al. |
| 6,659,933 B2 | 12/2003 | Asano |
| 6,673,006 B2 | 1/2004 | Winkler |
| 6,676,667 B2 | 1/2004 | Mareiro et al. |
| 6,685,619 B2 | 2/2004 | Halpern et al. |
| 6,692,460 B1 | 2/2004 | Jayaraman |
| 6,699,170 B1 | 3/2004 | Crocker et al. |
| 6,746,465 B2 | 6/2004 | Diederich et al. |
| 6,752,752 B2 | 6/2004 | Geitz |
| 6,910,999 B2 | 6/2005 | Chin et al. |
| 6,923,754 B2 | 8/2005 | Lubock |
| 6,955,641 B2 | 10/2005 | Lubock |
| 7,041,047 B2 | 5/2006 | Gellman et al. |
| 7,056,276 B2 | 6/2006 | Nakano et al. |
| 7,357,770 B1 | 4/2008 | Cutrer et al. |
| 7,413,539 B2 | 8/2008 | Lubock |
| 7,465,268 B2 | 12/2008 | Lubock |
| 2001/0007071 A1 | 7/2001 | Koblish |
| 2002/0016583 A1 | 2/2002 | Cragg |
| 2002/0032359 A1 | 3/2002 | Geoffrion et al. |
| 2002/0165427 A1 | 11/2002 | Yachia et al. |
| 2003/0092957 A1 | 5/2003 | Scott et al. |
| 2003/0114878 A1 | 6/2003 | Diederich et al. |
| 2003/0158515 A1 | 8/2003 | Gonzalez et al. |
| 2003/0163017 A1 | 8/2003 | Tam et al. |
| 2003/0236443 A1 | 12/2003 | Cespedes et al. |
| 2004/0006305 A1 | 1/2004 | Hebert et al. |
| 2004/0068231 A1 | 4/2004 | Blondeau |
| 2004/0087828 A1 | 5/2004 | Green et al. |
| 2004/0116767 A1 | 6/2004 | Lebovic et al. |
| 2004/0127765 A1 | 7/2004 | Seiler et al. |
| 2004/0260142 A1 | 12/2004 | Lovoi |
| 2005/0061533 A1 | 3/2005 | Lovoi et al. |
| 2005/0075662 A1 | 4/2005 | Pedersen et al. |
| 2005/0080313 A1 | 4/2005 | Stewart et al. |
| 2005/0090845 A1 | 4/2005 | Boyd |
| 2005/0096647 A1 | 5/2005 | Steinke et al. |
| 2005/0101823 A1 | 5/2005 | Linares et al. |
| 2005/0101860 A1 | 5/2005 | Patrick et al. |
| 2005/0124843 A1 | 6/2005 | Singh |
| 2005/0182286 A1 | 8/2005 | Lubock |
| 2005/0240074 A1 | 10/2005 | Lubock |
| 2006/0015166 A1 | 1/2006 | Kindlein et al. |
| 2006/0020156 A1 | 1/2006 | Shukla |
| 2006/0094923 A1 | 5/2006 | Mate |
| 2006/0100475 A1 * | 5/2006 | White et al. ..................... 600/3 |
| 2006/0116546 A1 | 6/2006 | Eng |
| 2006/0173233 A1 | 8/2006 | Lovoi |
| 2006/0173235 A1 | 8/2006 | Lim et al. |
| 2006/0184192 A1 | 8/2006 | Markworth et al. |
| 2006/0199990 A1 | 9/2006 | Rioux et al. |
| 2006/0235365 A1 | 10/2006 | Terwilliger et al. |
| 2006/0258895 A1 | 11/2006 | Maschke |
| 2007/0106108 A1 | 5/2007 | Hermann et al. |
| 2007/0142694 A1 | 6/2007 | Cutrer et al. |
| 2007/0167666 A1 | 7/2007 | Lubock |
| 2007/0167667 A1 | 7/2007 | Lubock et al. |
| 2007/0191668 A1 | 8/2007 | Lubock et al. |
| 2007/0276352 A1 * | 11/2007 | Crocker et al. ............... 604/500 |
| 2008/0091055 A1 | 4/2008 | Hermann |
| 2008/0221384 A1 * | 9/2008 | Chi Sing et al. ................. 600/7 |
| 2008/0228025 A1 | 9/2008 | Quick |
| 2009/0156882 A1 | 6/2009 | Chi Sing |
| 2009/0198095 A1 * | 8/2009 | Acosta et al. ..................... 600/3 |
| 2010/0048978 A1 | 2/2010 | Chi Sing |
| 2010/0331601 A1 | 12/2010 | Partridge |

* cited by examiner

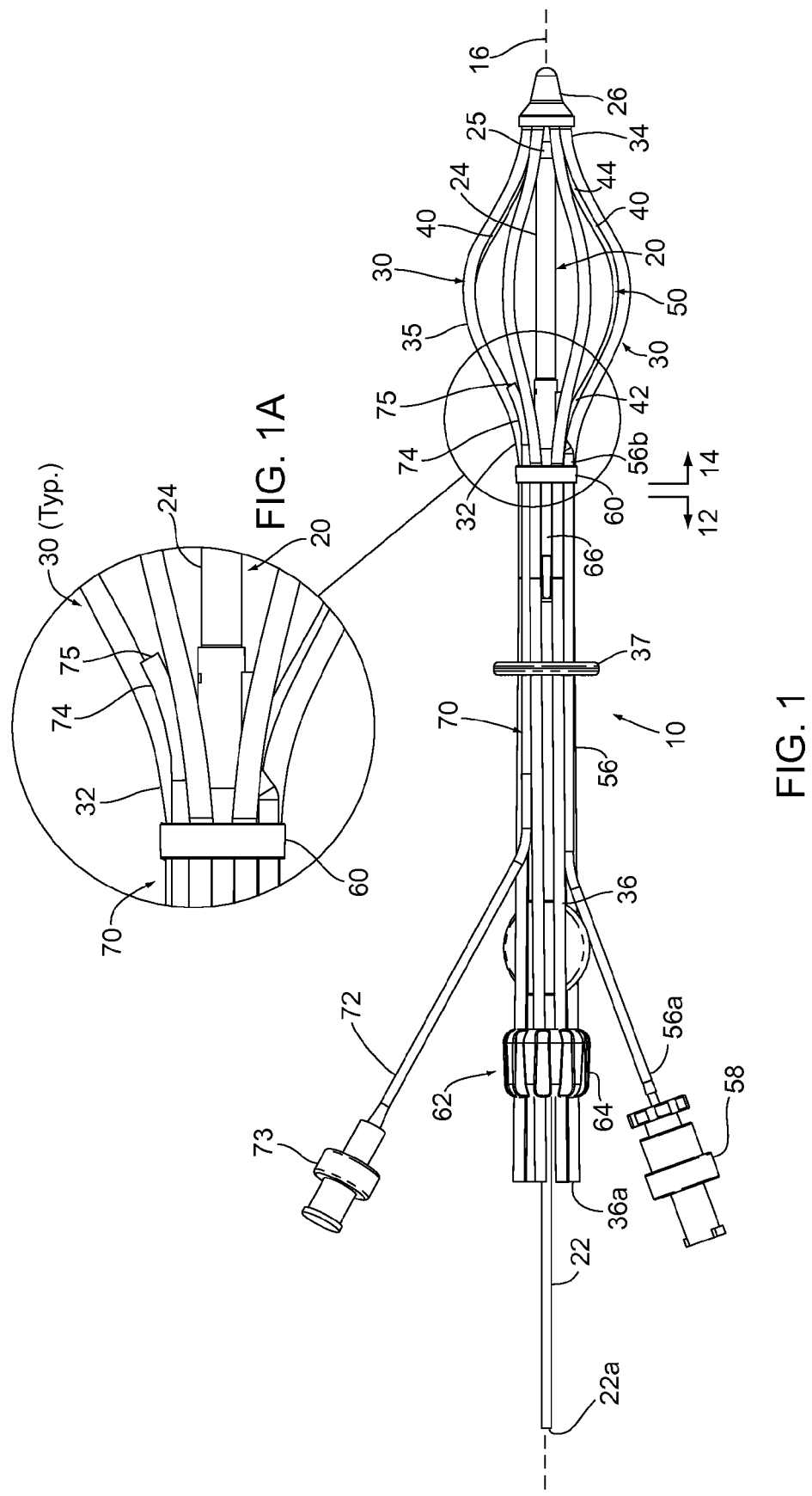

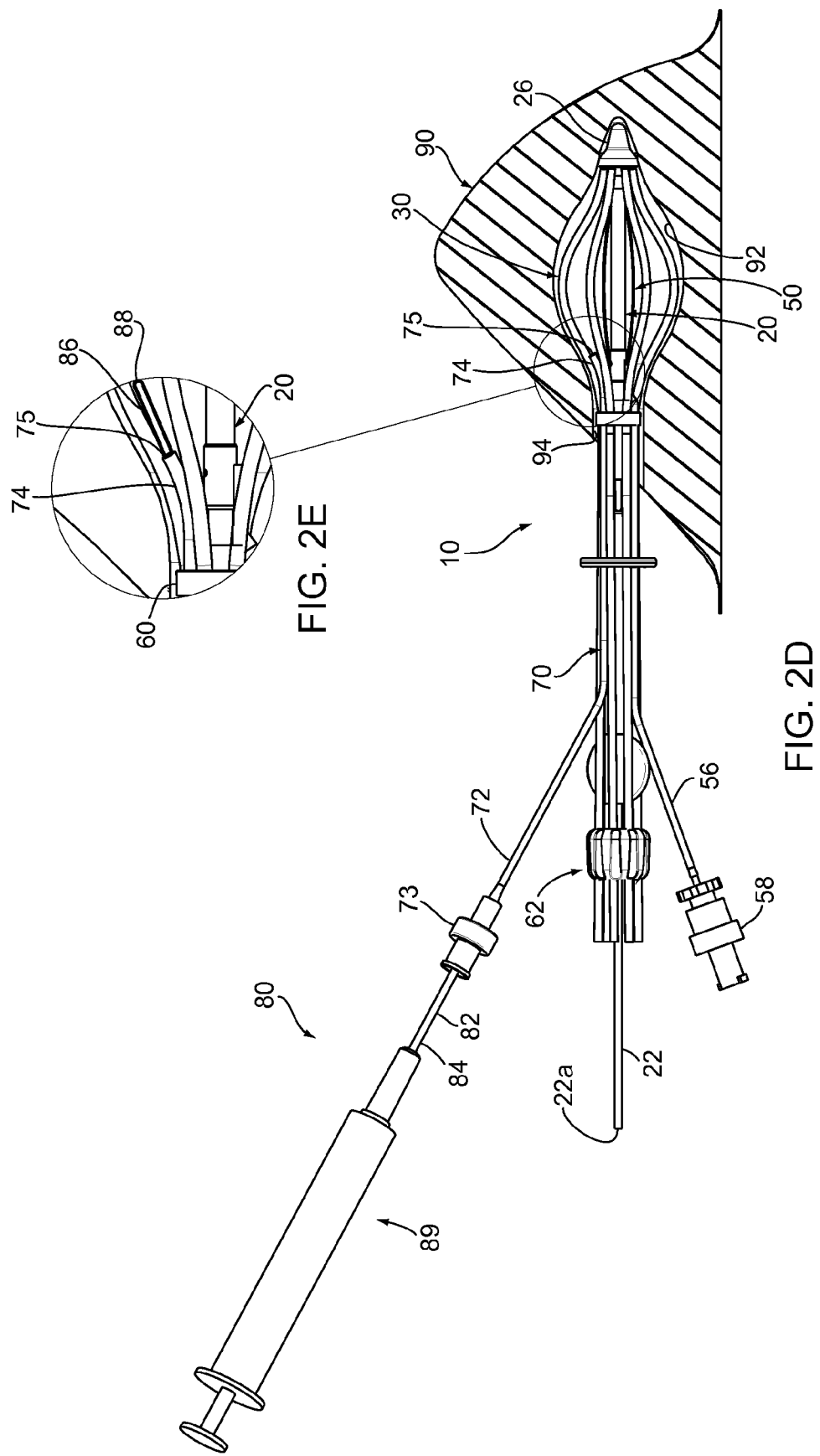

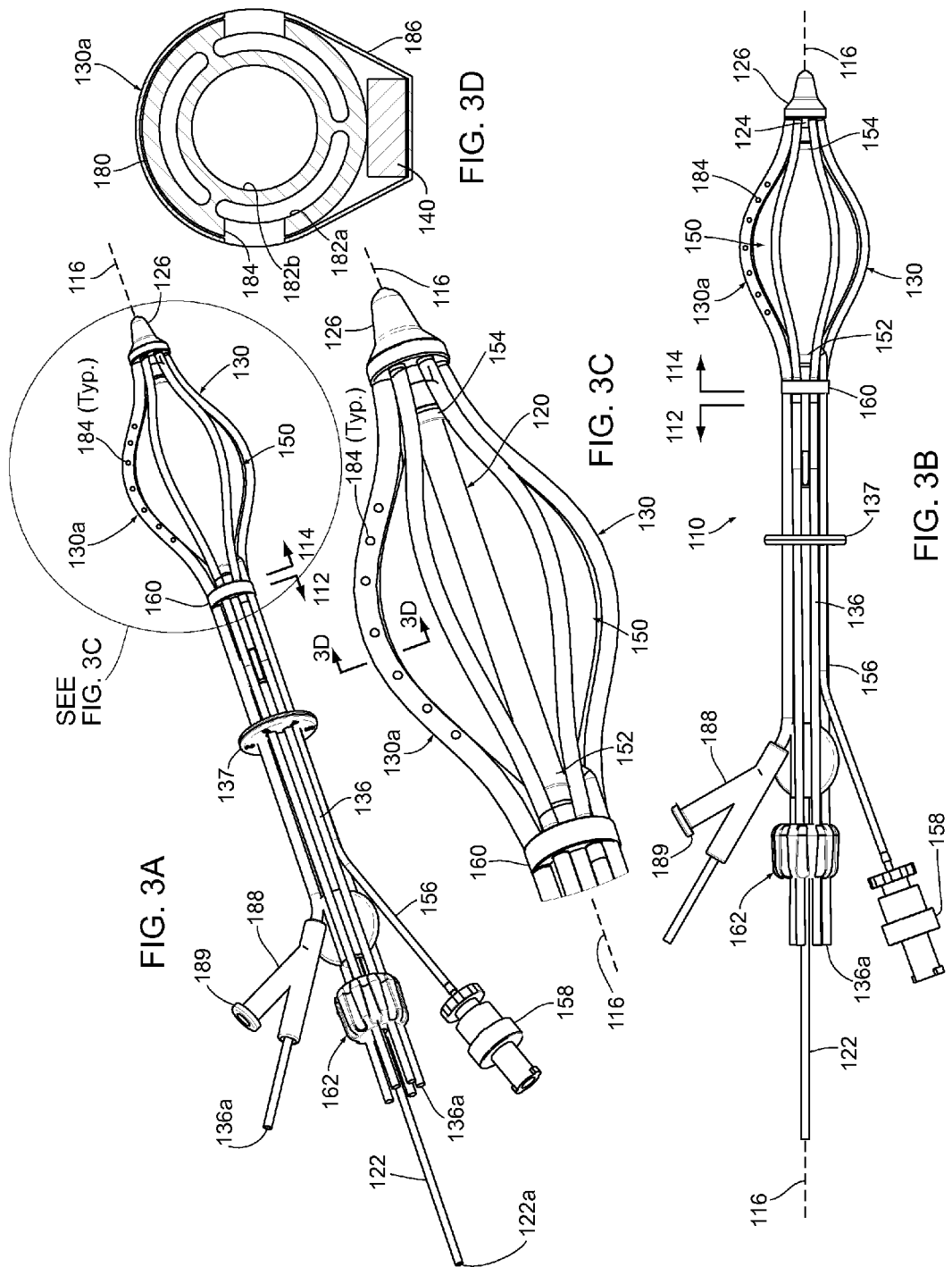

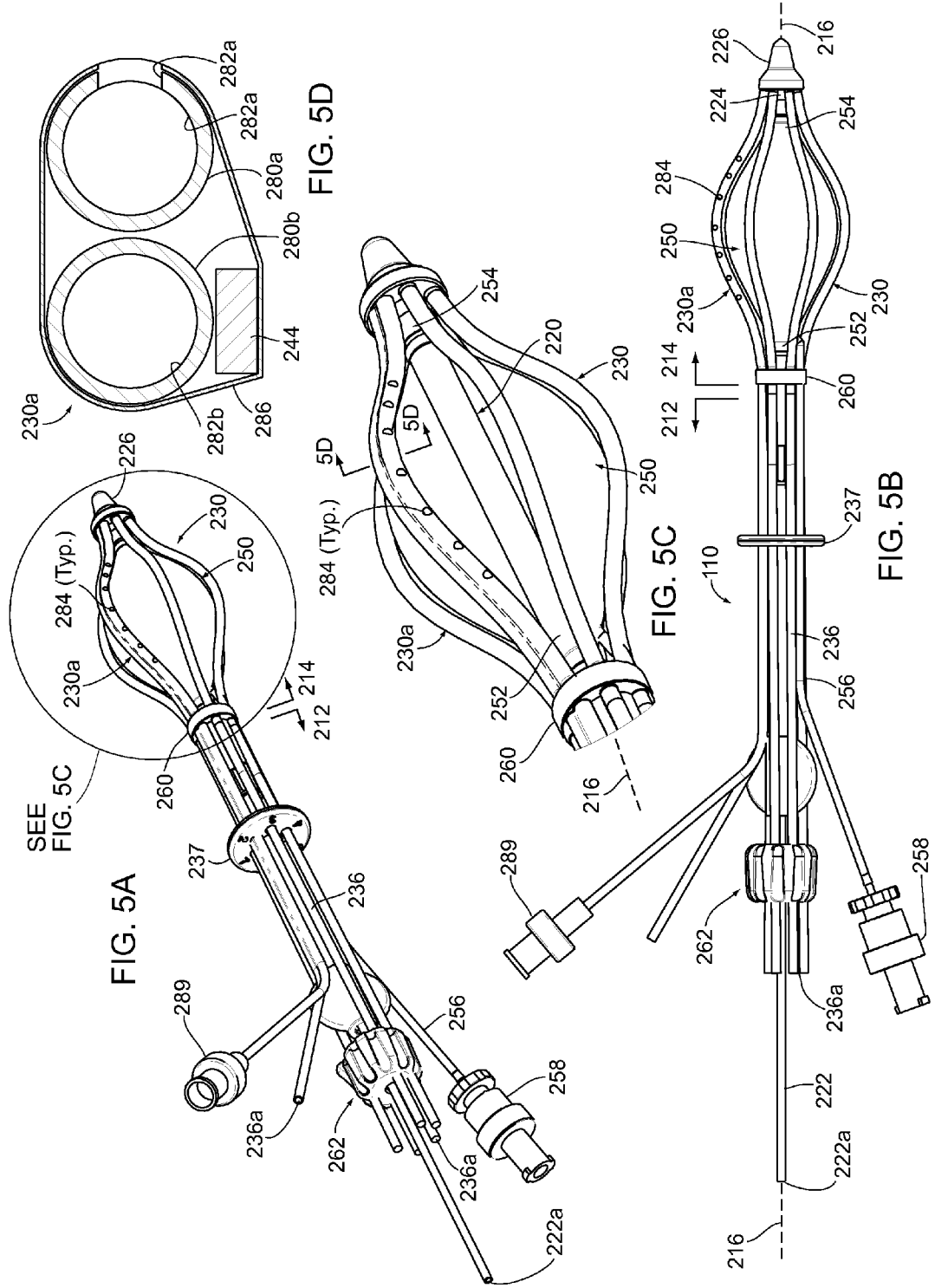

_US 9,067,063 B2_

EXPANDABLE BRACHYTHERAPY APPARATUS AND METHODS FOR USING THEM

FIELD OF THE INVENTION

The present invention relates generally to apparatus, systems, and methods for providing brachytherapy to a human or other mammalian body, and more particularly to expandable apparatus for performing brachytherapy treatment within tissue, e.g., within breast tissue and/or within a body cavity, and to methods for performing brachytherapy using such apparatus.

BACKGROUND

Brachytherapy is a type of radiation therapy used to treat malignant tumors, such as cancer of the breast or prostate. In general, brachytherapy involves positioning a radiation source directly into target tissue, e.g., a tumor and/or tissue surrounding a cavity or void, which may contain potentially cancerous cells (such as a cavity or void created by removing a tumor).

Brachytherapy is often divided into two categories: high dose rate (HDR) and low dose rate (LDR) brachytherapy. In HDR brachytherapy, a high activity radiation source is placed into target tissue, often via a previously implanted catheter, for a short period of time, e.g., lasting from several seconds to a few minutes. In LDR brachytherapy, a low activity radiation source is placed into the target tissue for a longer, sometimes indefinite, period of time.

Both forms of brachytherapy have advantages. For instance, HDR brachytherapy provides higher radiation levels delivered over a shorter dose delivery period, while LDR brachytherapy utilizes relatively lower activity radiation sources. The energy field of the LDR radiation source results in a measured and localized dose of radiation delivered to target tissue, e.g., a tumor, gland, or other tissue surrounding a cavity or void. However, the energy field thereafter decays to avoid excessive exposure of nearby healthy tissue. Due in part to the lower activity of LDR radiation sources, exposure precautions for LDR brachytherapy, e.g., for healthcare workers, may be less stringent than those for HDR brachytherapy. For patients, the relatively longer implantation period associated with LDR brachytherapy may result in fewer visits to a healthcare facility over the course of radiation treatment, as compared to HDR brachytherapy where patients must return to the healthcare facility for each fraction of radiation delivered, which, for breast brachytherapy, may typically include eight to ten (8-10) fractions.

While effective, current brachytherapy implementations have potential drawbacks. For example, LDR seeds are typically left indwelling and free floating within the target tissue and are, therefore, susceptible to migration. Moreover, once implanted, LDR seeds are generally not considered removable or repositionable. Yet another issue with conventional LDR brachytherapy techniques is that they may require the radioactive seeds to be manipulated individually at the time of implantation, which may be a time-consuming process. Moreover, conventional LDR delivery needles are generally limited to delivering the seeds linearly (along a relatively straight line). Thus, to achieve a desired therapy profile, numerous implants (e.g., including about 50-100 seeds, as are common with prostate brachytherapy) are often required, in conjunction with potentially complex dose distribution and mapping techniques and equipment.

SUMMARY

The present invention is generally directed to apparatus, systems, and methods for delivering brachytherapy to a localized target tissue region. While potentially useful in treating most any area of the body, an exemplary application is treating breast tissue, e.g., breast tumors or lumpectomy cavities. For example, the apparatus may be used to place and remove a localized radiation source for both neoadjuvant and post-excisional treatment.

In accordance with one embodiment, a system is provided for delivering one or more therapeutic elements (e.g., radiation sources) relative to a target tissue region. Once delivered, the radiation sources may be either immediately withdrawn (e.g., in HDR applications), or left in place, e.g., implanted, for a defined period of time (e.g., in LDR applications). In either instance, the radiation sources may deliver therapy to the target tissue region in accordance with a predefined therapy profile.

As used herein, "radiation source" or "source of radiation" may include any therapeutic element operable to deliver a dose of radiation. For example, the radiation source may be one or more radioactive seeds or, alternatively, one or more LDR or HDR wire elements (e.g., Iridium wire), e.g., as disclosed in the applications incorporated by reference elsewhere herein.

The term "implantable," as used herein, indicates the capability of a device to be inserted into the body and then maintained in a relatively fixed or static position within the surrounding tissue for an extended period of time, e.g., an hour or more and/or several hours or more, including several days or more.

Furthermore, "target tissue region," as used herein, may include any portion of a human (or other mammalian) body that has been identified to benefit from radiation therapy. For example, the target tissue region may be a tumor or lesion itself, tissue proximate or surrounding the tumor, or a cavity region created by tumor excision (such as the surrounding tissue or cavity associated with a lumpectomy cavity of the breast).

It should be noted that the apparatus, systems, and methods described herein may be used for LDR or HDR brachytherapy, as described elsewhere herein and in the applications incorporated by reference elsewhere herein. Moreover, while described herein with respect to brachytherapy, the apparatus, systems, and methods may apply to other therapy regimens that benefit from the removable implantation of therapy-delivering elements. In an exemplary application, the apparatus, systems, and methods are described herein for treating breast cancer. However, it will be appreciated that the apparatus, systems, and methods described herein may be used for treating other cancers or conditions that may benefit from brachytherapy treatment.

In accordance with one embodiment, a brachytherapy treatment apparatus is provided that includes an elongate body including a proximal portion and a distal portion sized for introduction into a tract through tissue. One or more tubular or elongate members may be provided on the distal portion including lumen(s) or other pathway(s) for receiving a source of radiation therealong, the elongate member(s) being movable between a collapsed configuration for introduction through a tissue tract to a target location and an expanded configuration. A source of radiation may be introduceable along the pathway(s) for delivering radiation to the target location.

For example, in one embodiment, the apparatus includes an elongate core member including proximal and distal ends, a proximal portion, and a distal portion configured for introduction into a tract through tissue and terminating in a distal tip. A plurality of catheters or other elongate members are provided on at least the distal portion adjacent the core member. Each elongate member may include a distal end coupled to the core member distal end, a proximal end movable relative to the core member, and a pathway extending between the elongate member proximal and distal ends for receiving a source of radiation therealong. Optionally, the core member may also include a source lumen or other pathway for receiving a source of radiation therealong.

The elongate member proximal ends may be movable relative to the distal ends for expanding the elongate members from a collapsed configuration to an expanded configuration such that the elongate members are directed radially outwardly away from the distal portion of the core member. For example, the apparatus may include a proximal hub movably mounted on the core member and the proximal ends of the elongate members may be coupled to the proximal hub such that an actuator member extending proximally from the proximal hub may be used for actuating the proximal hub to direct the elongate members from the collapsed configuration to the expanded configuration.

In addition, the apparatus may include an expandable member including a proximal end coupled to the core member adjacent the elongate member proximal ends and a distal end coupled to the distal tip of the core member such that the expandable member surrounds the distal portion of the core member. For example, the proximal and distal ends of the expandable member may be coupled to the core member at spaced apart locations or to proximal and distal hubs on the core member such that an interior of the expandable member is substantially sealed to allow introduction of inflation media therein to expand the expandable member. In an exemplary embodiment, the expandable member may be a balloon or other impermeable membrane and the apparatus may include an inflation lumen extending distally from the core member proximal end and communicating with the interior of the expandable member for delivering inflation media into and withdrawing inflation media from the interior for expanding and collapsing the expandable member.

The elongate members may extend along an outer surface of the expandable member in the collapsed configuration. The expandable member may be expandable independently of the elongate members such that the elongate members may be expanded away from the expandable member before the expandable member is expanded. Thus, the expandable member may be expanded after expanding the elongate members such that the expandable member expands outwardly towards and/or contacts the expanded elongate members, e.g., to facilitate imaging and/or other aspects of a treatment procedure.

Optionally, the apparatus may also include a working channel member extending between the proximal and distal portions of the core member. The working channel member may include a lumen extending therethrough, for example, for directing one or more instruments into a cavity or other region adjacent the distal portion, e.g., outside the expandable member. If desired, the working channel member may include a valve for selectively sealing the lumen, e.g., to prevent leakage of fluid from the cavity or region while accommodating introducing the one or more instruments therethrough.

In an exemplary embodiment, the one or more instruments may include an aspiration catheter for aspirating material from within the cavity or other region adjacent the distal portion. For example, the aspiration catheter may include a proximal end, a distal end sized for introduction through the working channel, and a lumen extending therebetween. The aspiration catheter proximal end may be coupled to a vacuum source for aspirating material into the aspiration catheter lumen via an opening in the aspiration catheter distal end.

In another option, at least one of the elongate members may include an aspiration member including one or more ports adjacent the distal portion communicating with an aspiration lumen extending to a proximal end of the aspiration member. A vacuum source may be coupled to the proximal end of the aspiration member for aspirating material into the aspiration lumen via the one or more ports. In one embodiment, the aspiration member may be disposed adjacent a tubular member including a source lumen or other pathway for receiving a source of radiation therealong. In another embodiment, the aspiration member may also include a source lumen, in addition to the aspiration lumen, e.g., providing a pathway for receiving a source of radiation therealong.

In accordance with another embodiment, a brachytherapy treatment apparatus is provided that includes an elongate core member including proximal and distal ends, a proximal portion, and a distal portion configured for introduction into a tract through tissue and terminating in a distal tip. A plurality of catheters or other elongate members are provided on at least the distal portion adjacent the core member. Each elongate member may include a distal end coupled to the core member distal end, a proximal end movable relative to the core member, and a pathway extending between the elongate member proximal and distal ends for receiving a source of radiation therealong.

The elongate member proximal ends may be movable relative to the distal ends for expanding the elongate members from a collapsed configuration to an expanded configuration such that the elongate members are directed radially outwardly away from the distal portion of the core member. For example, the apparatus may include a proximal hub movably mounted on the core member and the proximal ends of the elongate members may be coupled to the proximal hub such that an actuator member extending proximally from the proximal hub may be used for actuating the proximal hub to direct the elongate members from the collapsed configuration to the expanded configuration.

An aspiration device may be provided for removing material from a cavity or other region within which the proximal portion may be introduced. For example, at least one of the elongate members may include an aspiration member including one or more ports adjacent the distal portion communicating with an aspiration lumen extending to a proximal end of the aspiration member. Alternatively, the apparatus may include a working channel extending between the proximal and distal portions of the core member for receiving one or more instruments, e.g., an aspiration catheter for aspirating material from within the cavity or region adjacent the distal portion.

Optionally, the apparatus may include an expandable member including a proximal end coupled to the core member adjacent the elongate member proximal ends and a distal end coupled to the distal tip of the core member such that the expandable member surrounds the distal portion of the core member. In an exemplary embodiment, the expandable member may be a balloon or other impermeable membrane and the core member may include an inflation lumen extending distally from the core member proximal end and communicating with the interior of the expandable member for delivering inflation media into the interior for expanding the expandable member.

In accordance with yet another embodiment, a brachytherapy treatment apparatus is provided that includes an elongate core member comprising proximal and distal ends, a proximal portion, and a distal portion configured for introduction into a tract through tissue and terminating in a distal tip; a distal hub coupled to the distal tip of the core member; a proximal hub movably mounted on the core member proximal to the distal hub; and a plurality of elongate catheters including distal ends coupled to the distal hub, proximal ends coupled to the proximal hub, elongate portions that extend between the proximal and distal hubs, and lumens extending between the respective catheter proximal and distal ends for receiving a source of radiation therealong. At least one of the catheters may include an aspiration member including one or more ports adjacent the distal portion communicating with an aspiration lumen extending to a proximal end of the aspiration member. An actuator member may be coupled to and extend proximally from the proximal hub, the actuator member being actuatable for moving the catheters from a collapsed configuration to an expanded configuration such that the elongate portions are directed radially outwardly away from the core member.

In addition, the apparatus may include an expandable member including a proximal end coupled to the core member and/or proximal hub and a distal end coupled to the core member and/or distal hub such that the expandable member surrounds the distal portion of the core member, the elongate members extending along an outer surface of the expandable member in the collapsed configuration In accordance with still another embodiment, a method is provided for brachytherapy treatment of tissue surrounding a cavity within a target location of a body. A distal portion of an elongate body, including a core member defining a central axis and carrying a plurality of elongate members, may be advanced into the cavity with the elongate members in a collapsed configuration, and the elongate members may be directed to an expanded configuration within the cavity to position portions of the elongate members away from the central axis and adjacent tissue surrounding the cavity.

An expandable member on the distal portion between the core member and the elongate members may be expanded outwardly towards the expanded elongate members, e.g., by delivering inflation media into an interior of the expandable member. In one embodiment, the inflation media may include water, gel, contrast media, fluids, and/or other flowable materials that are compatible with external imaging modes, such as ultrasound or CT (computerized tomography) scanning. At least the distal portion of the elongate body and tissue surrounding the cavity may be imaged, for example, using external ultrasound or CT scanning, to facilitate visualization of the expanded elongate members and core member relative to the surrounding tissue, e.g., to verify conformance of the expanded distal portion to the geometry of the cavity. In addition, the expanded expandable member may aid in developing a dose plan for treating the target location, e.g., by delineating the position of the surrounding tissue relative to the elongate members. After imaging, the expandable member may be collapsed, radiation may be delivered to the target location via the elongate members and/or core member to treat tissue at the target location, e.g., in accordance with the dose plan. Alternatively, the expandable member may remain expanded during treatment, e.g., between fractions of a multiple treatment plan, which may facilitate maintaining the surrounding tissue in a substantially defined position relative to the elongate members and core member throughout the treatment.

The above summary is not intended to describe each embodiment or every implementation of the present invention. Rather, a more complete understanding of the invention will become apparent and appreciated by reference to the following detailed description and claims in view of the accompanying drawings.

BRIEF DESCRIPTION OF THE DRAWINGS

The drawings illustrate exemplary embodiments, in which:

FIG. 1 is a side view of a first exemplary embodiment of an expandable brachytherapy apparatus including a plurality of catheters in an expanded configuration.

FIG. 1A is a detail of a hub on a distal end of the apparatus of FIG. 1 showing an outlet of a working channel provided on the apparatus.

FIG. 2D is a cross-sectional view of the breast of FIGS. 2A-2C, showing the balloon deflated and an aspiration catheter being introduced into the cavity via the working channel.

FIG. 2E is a detail of the apparatus of FIG. 2D, showing a tip of the aspiration catheter being deployed with the cavity.

FIGS. 3A and 3B are perspective and side views, respectively, of a second exemplary embodiment of an expandable brachytherapy apparatus including a plurality of catheters in an expanded configuration.

FIG. 3C is a detail of a distal end of the catheters of the apparatus of FIGS. 3A and 3B showing the catheters in the expanded configuration and including an aspiration catheter.

FIG. 3D is a cross-sectional view of the aspiration catheter of FIG. 3C taken along line 3D-3D.

FIGS. 5A and 5B are perspective and side views, respectively, of a third exemplary embodiment of an expandable brachytherapy apparatus including a plurality of catheters in an expanded configuration.

FIG. 5C is a detail of a distal end of the catheters of the apparatus of FIGS. 5A and 5B showing the catheters in the expanded configuration and including an aspiration catheter.

FIG. 5D is a cross-sectional view of the aspiration catheter of FIG. 5C taken along line 5D-5D.

DETAILED DESCRIPTION OF EXEMPLARY EMBODIMENTS

Figure 2A:
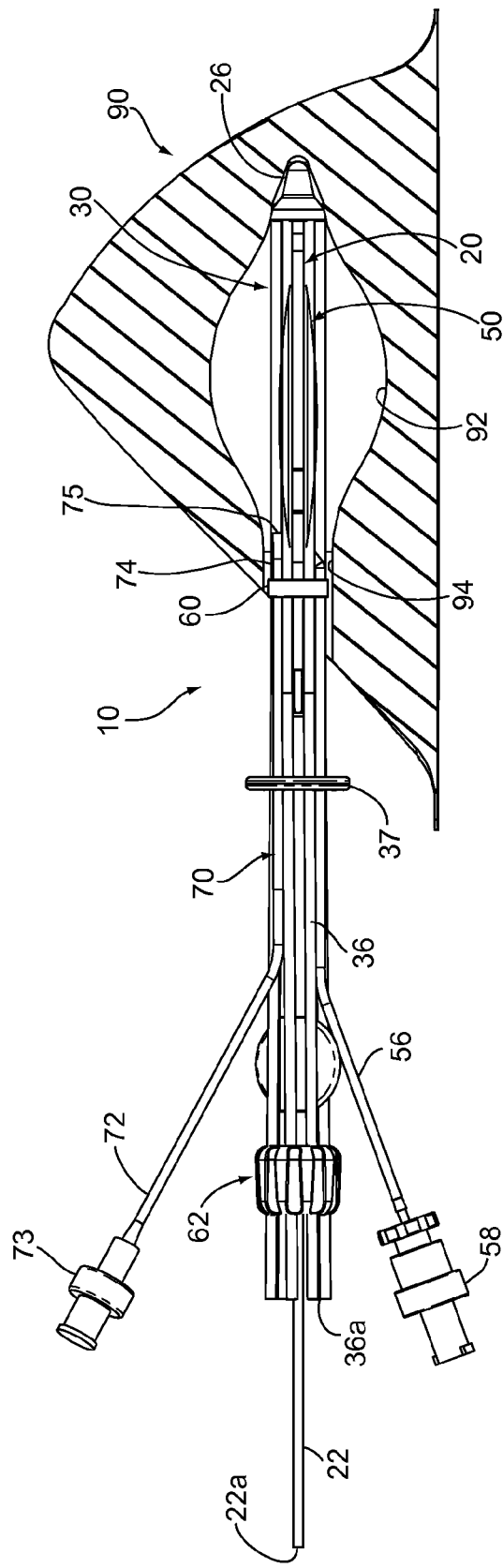
FIGS. 2A and 2B are cross-sectional views of a breast, showing the apparatus of FIG. 1 being introduced into a lumpectomy cavity in the breast with the catheters in a collapsed configuration (FIG. 2A) and expanded to the expanded configuration (FIG. 2B).
Figure 2B:
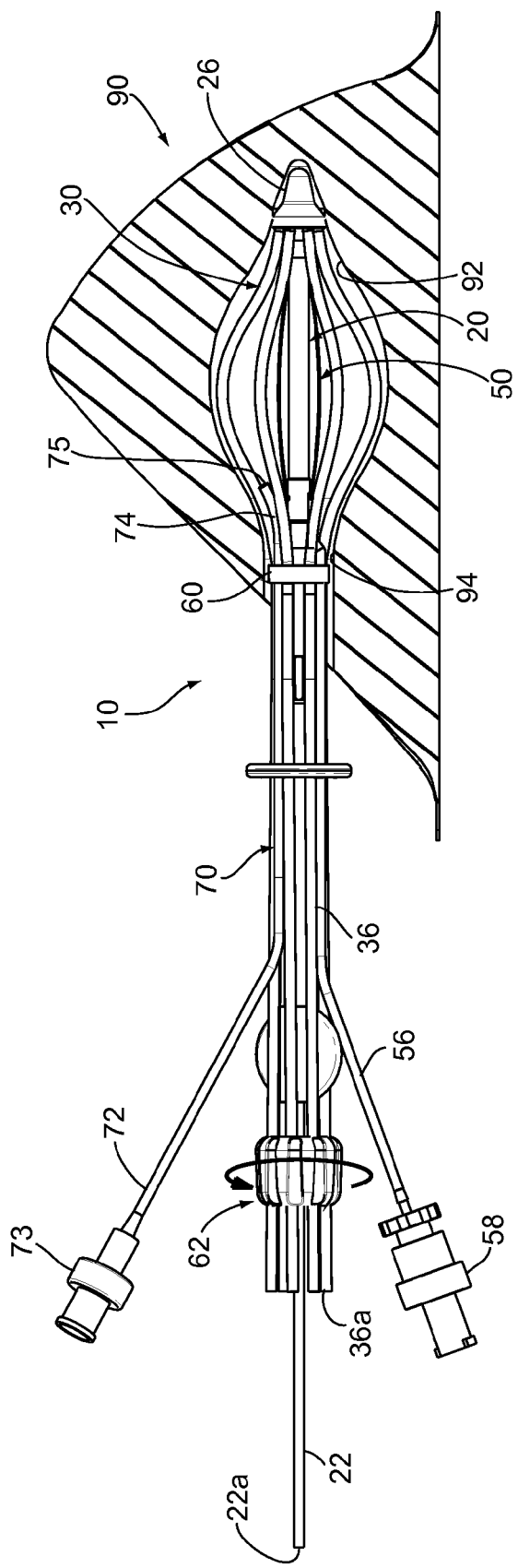

Turning to the drawings, FIG. 1 shows an exemplary embodiment of an expandable brachytherapy apparatus 10 that includes a proximal or tail portion 12, and a distal or therapy delivery portion 14, generally defining a longitudinal axis 16 extending therebetween. As described further below, the distal portion 14 may be deployed or introduced within a target location of a patient's body, e.g., a tumor or cavity within a breast or other body structure (not shown), and the proximal portion 12 may extend from the distal portion 14, e.g., such that the proximal portion 12 protrudes at least partially outside of the body structure. The distal portion 14 generally includes an elongate core member 20, one or more catheters or other elongate members 30 adjacent the core member 20, and a balloon or other expandable member 50 (shown in cross-section only for clarity) at least partially surrounding the core member 20. The elongate members 30 may be movable between a collapsed configuration, as shown in FIG. 2A, e.g., for introduction through a tissue tract to a target location, and a fully deployed or expanded configuration, as shown in FIG. 2B, e.g., for providing a three dimensional array of pathways at the target location, as described further below. The expandable member 50 may be expandable independently of the elongate members 30, e.g., to facilitate imaging, delineation of tissue surrounding a target treatment location, and the like, also as described further below.

In addition or alternatively, the apparatus 10 may be part of a system, e.g., including a tubular delivery device, such as an introducer sheath, catheter, cannula, trocar, obturator, and/or needle (not shown), for introducing the apparatus 10 into a target location, one more sources of radiation, an aspiration catheter, and/or other components (also not shown), as described elsewhere herein and in the applications incorporated by reference elsewhere herein.

In the embodiment shown in FIG. 1, the core member 20 includes a proximal end 22 and a distal end 24 terminating in a distal tip 25, a distal hub 26 coupled to the distal tip 25, and a proximal hub 60 movable relative to the core member 20. Optionally, the core member 20 may include a source lumen therein, e.g., extending from an opening 22a in the proximal end 22 to the distal end 24. The elongate members 30 extend generally axially adjacent the core member 20 in the collapsed configuration, e.g., between the proximal and distal hubs 60, 26.

For example, as shown, six elongate members 30 are provided that include proximal ends 32 coupled to the proximal hub 60, distal ends 34 coupled to the distal hub 26, and expandable intermediate portions 35 adjacent the core member 20. As shown, the elongate members 30 may be offset circumferentially from one another about the longitudinal axis 16, e.g., about sixty degrees (60°). The elongate members 30 extend substantially axially along the core member 20 in the collapsed configuration and may bow or curve radially outwardly away from the core member 20 in the expanded configuration. It will be appreciated that, although six elongate members 30 are shown, fewer or additional elongate members 30 may be provided, e.g., three, four, five, seven, eight, or more (not shown), with the elongate members 30 offset radially relative to one another, e.g., distributed substantially evenly about the perimeter of the core member 20.

The distal hub 26 may be formed from one or more components integrally molded, machined, or otherwise formed together from a single piece, or as separate components that are attached together. The distal ends 34 of the elongate members 30 may be received within and/or otherwise secured to the distal hub 26, e.g., by bonding with adhesive, sonic welding, fusing, mating connectors, and the like. The distal hub 26 may provide a rounded and/or tapered distal tip for the apparatus 10, e.g., to facilitate substantially atraumatic introduction into a patient's body. Alternatively, the distal hub 26 may include a pointed or other sharpened distal tip (not shown) for facilitating advancing the apparatus 10 directly through tissue, e.g., by dissection or puncture through tissue between the patient's skin and a target location. Optionally, the distal hub 26 (and/or other components of the apparatus 10) may include radiopaque material, echogenic material, and the like to facilitate monitoring the distal hub 26 (and/or the apparatus 10) using external imaging, such as ultrasound, CT scanning or other x-ray imaging, and the like.

The proximal hub 60 may be provided from one or more pieces, e.g., that may be slidably mounted around the core member 20 and coupled to the proximal ends 32 of the elongate members 30. For example, the proximal hub 60 may include an annular collar that includes nipples or passages (not shown) for receiving the proximal ends 32 of the elongate members 30 to substantially permanently attach the proximal ends 32 to the proximal hub 60, e.g., by interference fit. In addition or alternatively, the proximal ends 32 may be attached to the proximal hub 60 by bonding with adhesives, sonic welding, fusing, cooperating connectors, and the like. Alternatively, the proximal hub 60 may be formed from separate components (not shown) that may be attached together around the core member 20, e.g., using an interference fit, cooperating connectors, bonding using adhesive, sonic welding, and the like.

The elongate members 30 may be elongate, fixed length tubular members or "catheters," each including a proximal end 32, a distal end 34, and a lumen (not shown) extending therebetween, e.g., along the expandable intermediate portion 35 that extends along the core member 20. The proximal ends 32 may be received in, through, and/or otherwise coupled to the proximal hub 60, e.g., as described elsewhere herein.

As shown, the elongate members 30 may include individual catheter tubes 30 coupled to respective struts or other supports 40. For example, the supports 40 may be elongate wires, strips of material, and the like, e.g., made from metal, such as stainless steel or Nitinol, plastic, or composite material, that may be elastically deflected during use of the apparatus 10, e.g., when the distal portion 14 is directed between the collapsed and expanded configurations. Generally, the supports 40 include a circumferential or transverse "width" and a radial "thickness," e.g., having a rectangular or elliptical cross-section to cause preferential bending of the supports 40 radially outwardly into an arcuate shape that bows radially outwardly from the proximal and distal hubs 60, 26. The supports 40 may have a substantially homogeneous cross-section along their lengths or may have varying cross-sections (not shown), e.g., if desired to vary the rigidity and/or bias of the elongate members 30 using the supports 40.

The supports 40 may extend at least partially along the intermediate portion 35 of the elongate members 30. For example, the proximal ends 42 of the supports 40 may be attached or secured to the proximal hub 60 and/or the proximal ends 32 of the elongate members 30, and the distal ends 44 may be attached or secured to distal hub 26 and/or the distal ends 34 of the elongate members 30. In an exemplary embodiment, the distal ends 44 may be integrally formed with a sleeve or collar (not shown) that may be received within, around, and/or otherwise secured to the distal hub 26, similar to the embodiments described in application Ser. No. 11/868, 483, filed Oct. 6, 2007, published as U.S. Publication No. 2008/0091055, the entire disclosure of which is expressly incorporated by reference herein. In addition, the proximal ends 42 may include connectors (not shown) that may be interlocked with one another and/or the proximal hub 60. Alternatively, the proximal ends 42 may be integrally formed with a collar or sleeve (not shown), similar to the distal ends 44.

The supports 40 may be oriented such that their major dimension or width is disposed generally circumferentially relative to the core member 20 and their minor dimension or thickness is disposed generally radially. The supports 40 may be attached or otherwise secured to the elongate members 30 at one or more locations along their lengths, e.g., using shrink tubing, bonding with adhesive, sonic welding, and the like. For example, heat shrink tubing (not shown) may be provided at one or more locations along the length of the elongate members 30 between the proximal and distal ends 32, 34 to couple movement of the elongate members 30 to the supports 40, e.g., as disclosed in application Ser. No. 12/277,286, filed Nov. 24, 2008, published as U.S. Publication No. 2009/0156882, the entire disclosure of which is expressly incorporated by reference herein.

Alternatively, the supports 40 may be provided within an additional lumen (not shown) within the elongate members 30, similar to embodiments disclosed in the applications incorporated by reference elsewhere herein. In a further alternative, the supports 40 may be eliminated. For example, the elongate members 30 themselves may be configured, e.g., may have asymmetrical cross-sections (not shown) providing a moment of inertia that biases the elongate members 30 to expand radially outwardly towards a predetermined arcuate shape, e.g., while minimizing lateral movement. Optionally, the supports 40 may provide shielding, in addition to or instead of supporting the elongate members 30, also as disclosed in the applications incorporated by reference elsewhere herein.

With continued reference to FIG. 1, tubular extensions 36 may be coupled to the proximal hub 60 and/or coupled directly to the proximal ends 32 of the elongate members 30, e.g., extending proximally from the proximal hub 60 to at least partially define the proximal portion 12 of the apparatus 10. For example, the tubular extensions 36 may be received in passages or over nipples (not shown) on the proximal hub 60 similar to the proximal ends 32 of the elongate members 30 such that lumens of the tubular extensions 36 communicate with lumens of the respective elongate members 30. As shown, each tubular extension 36 includes an opening 36*a* providing access into a respective source lumen, e.g., through the tubular extension 36 and into a respective elongate member 30, for receiving a radiation source, as described elsewhere herein. Alternatively, the tubular extensions 36 may be formed as an integral part of the elongate members 30, e.g., as a continuous extrusion, molding, and the like, such that the elongate members 30 extend continuously from the openings 33*a* to the distal ends 34.

The tubular extensions 36 may remain substantially free relative to one another or may be at least partially constrained relative to one another. For example, as shown, the tubular extensions 36 may extend substantially parallel to the longitudinal axis 16 along the core member 20 yet be sufficiently flexible to directed away from the core member 20, if desired during use. Optionally, the tubular extensions 36 may pass through or be captured by a collar or other structure 37 on the proximal portion 12 of the apparatus, thereby keeping the tubular extensions 36 together, organized, and/or otherwise limiting relative movement of the tubular extensions 36, similar to embodiments in the applications incorporated by reference herein. The collar 37 may be fixed axially relative to the tubular extensions 36 or may be slidable along the tubular extensions 36, if desired. Optionally, the collar 37 may be include numbers or other indicia (not shown) to identify respective openings 36*a*, tubular extensions 36, and/or source lumens during use.

Generally, the tubular extensions 36 may be flexible, e.g., to allow the tubular extensions 36 to be curved or otherwise bent individually and/or together. Thus, the proximal portion 12 of the apparatus 10 may be easily bent, e.g., to accommodate securing the proximal portion 12 to a patient, for example, to the patient's skin adjacent a tract communicating with a treatment site within which the distal portion 14 has been introduced. Optionally, the tubular extensions 36 may include one or more features, such as those disclosed in the applications incorporated by reference herein, to enhance flexibility and/or bending of the tubular extensions 36 to minimize a profile of the proximal portion 12 of the apparatus 10.

Similarly, the core member 20 may include one or more regions between the proximal and distal ends 22, 24 constructed from different materials and/or methods, e.g., to provide desired flexibility or rigidity for the proximal and distal portions 12, 14 of the apparatus 10. For example, the distal end 24 may include one or more substantially rigid tubular bodies, e.g., extending at least between the proximal and distal hubs 60, 26 to maintain the relative position of the proximal and distal hubs 60, 26 and/or provide sufficient support for the elongate members 30 as they are expanded and/or collapsed. The proximal end 22 may include one or more semi-rigid or substantially flexible tubular members, e.g., similar to the extensions 36, to allow the proximal end 22 to be bent, folded, or otherwise directed against a patient's skin, e.g., while the distal end 24 is positioned within a target tissue region, as described elsewhere herein.

With continued reference to FIG. 1, an actuator member 62 may extend proximally from the proximal hub 60 for controlling movement of the proximal hub 60 from the proximal portion 12 of the apparatus 10. For example, as shown, the actuator member 62 includes an elongate sleeve or tubular body including a proximal end 64 adjacent the proximal end 22 of the core member 20 and a distal end 66 coupled to the distal end 14 of the core member 20 and/or the proximal hub 60. The sleeve 62 may be movably disposed around the proximal end 22 of the core member 20 such that the sleeve 62 may be rotated and/or directed axially to move the proximal hub 60 to expand and/or collapse the elongate members 30, as described further below.

In an exemplary embodiment, the distal end 24 of the core member 20 may include a pair of telescoping tubes (not shown) extending between the proximal and distal hubs 60, 26 such that rotation of the tubes relative to one another cause the proximal and/or distal hubs 60, 26 to move axially towards or away from one another, e.g., similar to the embodiments described in the applications incorporated by reference elsewhere herein. For example, the actuator member 62 may be coupled to one of the telescoping tubes (not shown) such that subsequent rotation of the actuator member 62 causes the telescoping tube to rotate relative to the other telescoping tube, thereby directing the proximal hub 60 axially towards or away from the distal hub 26. Alternatively, the actuator member 62 may be coupled to the proximal hub 60, and the actuator member 62 and proximal hub 60 may be movable axially relative to the core member 20, e.g., similar to embodiments disclosed in application Ser. No. 12/727,209, filed Mar. 18, 2010, and Ser. No. 12/841,111, filed Jul. 21, 2010, the entire disclosures of which are expressly incorporated by reference herein. Thus, in this alternative, the actuator member 62 may be directed axially (distally or proximally without rotation) to direct the proximal hub 60 axially relative to the distal hub 26 to expand and collapsed the elongate members 30.

Optionally, at least a portion of the actuator member 62 may be removable from the apparatus 10. For example, the distal end 66 of the actuator member may be releasably coupled to the core member 20 and/or the proximal hub 60, e.g., by mating threads, detents, male-and-female keyed connectors, and/or other features (not shown). During manufacturing, the actuator member 62 may provided separately from the rest of the apparatus 10 or may already be coupled to the core member 20. If separate, before use, the actuator member 62 may be inserted between the tubular extensions 36 and over the proximal end 22 of the core member 20 until the distal end 66 is disposed adjacent the proximal hub 60. Connector(s) on the distal end 66 and the proximal hub 60 or one of the telescoping tubes may then be engaged to couple subsequent movement (e.g., rotation, linearly axial movement) of the proximal hub 60 to the actuator member 62 in preparation for use.

With continued reference to FIG. 1 and additional reference to FIGS. 2A-2D, the apparatus 10 also includes a balloon, impermeable membrane, or other expandable member 50 on the distal portion 14, extending at least partially between the proximal and distal hubs 60, 26. As shown, the expandable member 50 may be disposed between the elongate members 30 and the core member 20, e.g., such that the elongate members 30 extend along or around an outer surface of the expandable member 50. Alternatively, the balloon 50 may be disposed around the elongate members 30 (not shown), e.g., similar to embodiments in the applications incorporated by reference elsewhere herein.

Figure 2C:
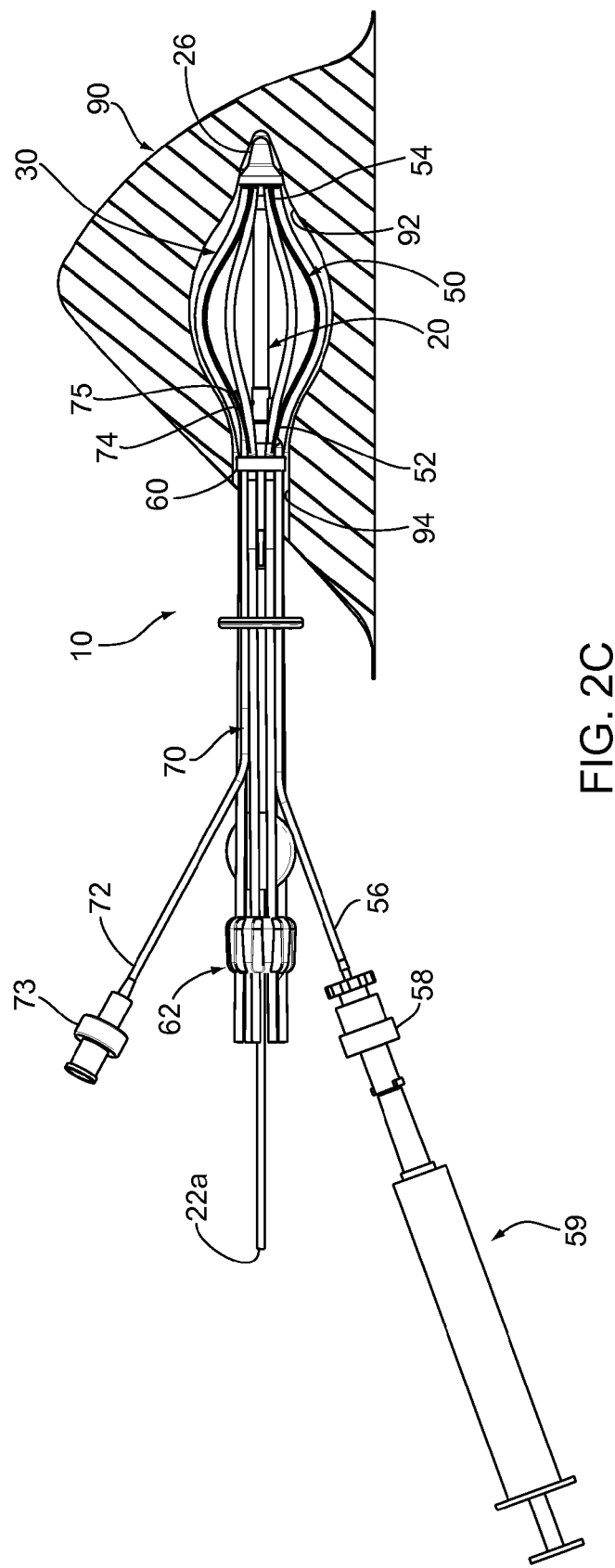
FIG. 2C is a cross-sectional view of the breast of FIGS. 2A and 2B, showing a balloon on the apparatus inflated within the cavity.

As best seen in FIG. 2C, the expandable member 50 includes a distal end 54 coupled to the core member 20, e.g., immediately adjacent the distal hub 26, or alternatively coupled directly to the distal hub 26, and a proximal end 52 coupled to the core member 20 at a predetermined distance proximal to the distal end 54. For example, the proximal end 52 of the expandable member 50 may be attached at a predetermined location on the core member 20 such that the proximal end 52 is disposed adjacent the proximal hub 60 and/or the proximal ends 32 of the elongate members 30 when the proximal hub 60 is advanced to direct the elongate members 30 to the expanded configuration. Alternatively, if the expandable member 50 is formed from elastic material, the proximal end 52 of the expandable member 50 may be attached or otherwise coupled to the proximal hub 60 (not shown), e.g., such that the length of the expandable member 50 changes as the proximal hub 60 is directed axially along the core member 20.

In an exemplary embodiment, the expandable member 50 may be formed from an annular membrane or other balloon structure and the proximal and distal ends 52, 54 of the balloon 50 may be attached to the core member 20 (or other component of the apparatus 10), e.g., by bonding with adhesive, sonic welding, fusing, overlying bands or collars, and the like. Thus, the proximal and distal ends 52, 54 may provide a substantially fluid tight seal to allow inflation media to be introduced into an interior of the balloon 50, i.e., between the balloon wall and the core member 20, to expand the balloon 50. The balloon 50 may be formed from substantially flexible or compliant material, e.g., such that the size of the balloon 50 is proportional to the amount of inflation media introduced into the interior of the balloon 50. Alternatively, the balloon 50 may be formed from non-compliant material, e.g., such that the balloon 50 may be expanded to a predetermined size and/or shape once sufficient fluid is introduced into the interior of the balloon 50 without substantially expanding further (until a rupture pressure is achieved within the balloon interior).

The apparatus 10 may include an inflation lumen 56 that extends at least partially between the proximal and distal portions 12, 14 thereof and communicates with the interior of the expandable member 50 for delivering inflation media into and/or evacuating inflation media from within the interior of the balloon 150. For example, the inflation lumen 56 may be a separate tubular member from the tubular extensions 36 and proximal end 22 of the core member 20, e.g., also captured by the collar 37 to facilitate organization of the various tubular members. The inflation lumen 56 may include a loose proximal end 56a including a Luer connector or other fitting 58 and a distal end 56b coupled to the core member 20 and/or proximal hub 60.

For example, the distal end 56b may extend through the proximal hub 60 and into the core member 20, which may include a lumen and one or more ports (not shown) communicating with the interior of the expandable member 50. Alternatively, the distal end 56b may extend through the proximal hub 60 and into the proximal end 52 of the balloon 50, e.g., such that an opening in the distal end 56b communicates with the interior of the expandable member 50. In a further alternative, if the proximal end 52 of the expandable member 50 is coupled to the proximal hub 60, the distal end 56b may be coupled to an opening through the proximal hub 60 that communicates with the interior of the expandable member 50.

A syringe 59 or other source of inflation media and/or vacuum may be coupled to the fitting 58, e.g., for delivering or evacuating inflation media into/from the inflation lumen 56 via the fitting 58, i.e., for inflating or collapsing the expandable member 50, as described further below. In exemplary embodiments, the inflation media may be a liquid, gel, contrast material, or other flowable material that may be compatible with ultrasound, CT scanning, or other imaging. Alternatively, the inflation media may be a gas, such as air, nitrogen, carbon dioxide, and the like.

As can be seen in FIGS. 2A-2D, the elongate members 30 may be expandable independently of the expandable member 50. For example, the actuator member 62 may be rotated in a first direction to direct the proximal hub 60 distally and expand the elongate members 30 from the collapsed configuration to the expanded configuration, as shown in FIG. 2B. Once the elongate members 30 are directed to the expanded configuration, the actuator member 62 may be secured in the distal position or simply removed, if desired, e.g., to prevent migration of the elongate members 30 towards the collapsed configuration.

At any desired time, the expandable member 50 may be expanded, e.g., by coupling the syringe 59 to the fitting 58, and introducing inflation media into the interior of the expandable member 50 via the inflation lumen 56. When fully inflated, the expandable member 50 may be spaced apart inwardly from at least a portion of the elongate members 30 or may contact the elongate members 30, e.g., to press surrounding tissue outwardly, as described further below. In an alternative embodiment, the expandable member 50 may be attached or otherwise coupled to the elongate members 30 (not shown), e.g., such that the expandable member 50 expands at least partially as the elongate members 30 are directed to the expanded configuration. If additional expansion of the expandable member 50 is desired, the expandable member 50 may then be inflated by directing inflation media into its interior.

Optionally, as shown in FIG. 1, the apparatus 10 may also include a working channel member 70 extending between the proximal and distal portions 12, 14 thereof. For example, as shown, the working channel member 70 includes a proximal end 72 including a valve, connector, or other fitting 73, a distal end 74 including an outlet 75, and a lumen or other working channel (not shown) extending therebetween. For example, the proximal end 72 may be captured by the collar 37 for organization but otherwise loose or free to be directed away from the tubular extensions 36 during use. The fitting 73 may include a valve (not shown) therein, which may substantially seal the lumen yet accommodate introduction of one or more instruments (not shown) into the lumen. For example, the fitting 73 may include a Luer valve, one-way valve, or other hemostatic valve that may slidably received one or more instruments therethrough while preventing substantial leakage of fluid through the fitting 73 around the instrument(s). In addition or alternatively, the fitting 73 may include a connector for positively engaging mating features on one or more instruments introduced into the fitting 73, e.g., to prevent the instrument(s) from moving once engaged, if desired during use.

The distal end 74 of the working channel member 70 may extend through or otherwise along the proximal hub 60 such that the opening 75 is disposed adjacent the elongate members 30 and/or expandable member 50. Optionally, as shown, the distal end 74 may be shaped, e.g., curved outwardly away from the core member 20, such that the distal end 74 does not interfere substantially with expansion of the expandable member 50 yet may place the opening 75 adjacent the outer surface of the expandable member 50. Optionally, the distal end 74 may include a valve (not shown) therein in addition to or instead of providing a valve in the fitting 73, e.g., to prevent fluid from leaking substantially into the working channel, if desired.

Turning to FIGS. 2A-2E, the apparatus 10 may be used for brachytherapy treatment within a tissue structure, for example, within a breast 90. As shown, the breast 90 may have a cavity (e.g., a lumpectomy cavity) 92 formed therein, e.g., by removal of cancerous tissue. If an introducer sheath is used (not shown), the introducer sheath may be introduced into the cavity 92, as described in the applications incorporated by reference elsewhere herein. For example, a trocar (also not shown) may be provided in the introducer sheath that includes a sharpened distal end, and the introducer sheath and trocar may be advanced directly through tissue, thereby creating a tract 94 communicating with the cavity 92. Alternatively, the tract 94 may be created in advance, e.g., using a needle or other device (not shown). The trocar may then be removed, leaving the introducer sheath to provide a path through the tissue of the breast 90 into the cavity 92. Optionally, if desired, the inner surface of the introducer sheath may include lubricious material to facilitate introducing the apparatus 10 and/or other devices therethrough.

With particular reference to FIG. 2A, the apparatus 10 may be provided initially with the proximal hub 60 and actuator member 62 in a proximal or first position, i.e., with the proximal and distal hubs 60, 26 spaced furthest apart, thereby providing the elongate members 30 in the collapsed condition. For example, the apparatus 10 may be manufactured with the elongate members 30 biased to the expanded configuration, e.g., by the supports 40, and the elongate members 30 may be collapsed to the collapsed configuration, e.g., before packaging and/or shipment. Alternatively, the apparatus 10 may be packaged and/or shipped with the elongate members 30 in the expanded configuration. Shortly before use, the actuator member 62 may be directed to collapse the elongate members 30 to the collapsed configuration. This alternative may be useful if the apparatus 10 may be stored for an extended time before use, e.g., to reduce the risk of the supports 40 losing some of their bias to the expanded configuration.

With continued reference to FIG. 2A, the apparatus 10 may be inserted through the tract 94, e.g., through an introducer sheath (not shown), with the elongate members 30 in the collapsed configuration, e.g., until the distal hub 26 is disposed within the cavity 92. Alternatively, the apparatus 10 may be inserted directly through an existing incision without an introducer sheath, e.g., the incision used to perform the lumpectomy, or via a new incision created for delivering the apparatus 10. In a further alternative, the apparatus 10 may be advanced directly through tissue, e.g., if the distal hub 26 includes a sharpened tip (not shown), as described in the applications incorporated by reference elsewhere herein.

During insertion, the apparatus 10 may be positioned such that the distal hub 26 is placed in the far end of the cavity 92, as shown in FIG. 2A, e.g., such that the elongate members 30 (in the collapsed configuration) extend across and/or partially from the cavity 92, e.g., into the tract 94. Once the apparatus 10 is positioned within the cavity 92, the introducer sheath (if used) may be removed from around the apparatus 10. For example, if the introducer sheath includes a longitudinal slit or is otherwise separable, the introducer sheath may be pulled transversely away from the apparatus 10, thereby causing side edges defining the slit to separate and pass around the apparatus 10 (not shown). As shown in FIG. 2A, with any introducer sheath (or other introducer device) completely removed, the distal portion 14 of the apparatus 10 is positioned within the cavity 92, with the proximal portion 12 extending from the cavity 92, through the tract 94, and/or otherwise out of the breast 90. Thus, the apparatus 10 is ready for expansion and delivery of radiation.

Turning to FIG. 2B, the actuator member 62 may be manipulated to direct the proximal hub 60 distally relative to the distal hub 26, thereby causing the elongate members 30 to expand outwardly within the cavity 92. For example, the actuator member 62 may be rotated to expand the elongate members 30 to the expanded configuration, which may lie within a range of diameters, e.g., depending on the size of the cavity 92 and/or the length and/or other configuration of the elongate members 30. When the apparatus 10 is directed to the expanded configuration, the elongate members 30 may have sufficient bias to at least partially direct tissue surrounding the cavity outwardly and/or cause the tissue to invaginate between adjacent elongate members 30, as disclosed in the applications incorporated by reference herein. Optionally, the elongate members 30 and/or the distal portion 14 may include one or more extensions, membranes, balloons, or other features to shape the cavity 92 in a desired manner, e.g., as described elsewhere herein and/or in the applications incorporated by reference herein.

In addition or alternatively, the elongate members 30 may have sufficient radial outward bias to maintain a desired maximum spacing between adjacent elongate members 30. For example, the supports 40 may bias the elongate members 30 to be spaced substantially uniformly from one another about the circumference when the apparatus 10 is expanded. In an exemplary embodiment, the maximum spacing of the supports 40, and consequently, the elongate members 30, may be not more than about 1.5 centimeters, e.g., at the midpoints of the supports 40.

Turning to FIG. 2C, once the elongate members 30 are directed to the expanded configuration, the expandable member 50 may be expanded, e.g., by coupling a syringe or other source of inflation media 59 to the fitting 58 and introducing inflation media into the interior of the expandable member 50. The inflation media may be compatible and/or enhance external imaging of the apparatus 10, cavity 92, and/or surrounding tissue. For example, air may interfere with ultrasound imaging, and so the inflation media may be a liquid, gel, or other flowable material that is does not interference with such imaging.

The expandable member 50 may be expanded until the expandable member 50 presses against or otherwise contacts the elongate members 30 and/or surrounding tissue. For example, the expandable member 50 may be expanded sufficiently to further shape the cavity 92 and/or surrounding tissue in addition to any shaping achieved with the elongate members 30 alone, and/or to substantially fill any voids or gaps within the cavity 92. Alternatively, the expandable member 50 may be expanded until it is spaced slightly away from the elongate members 30, e.g., simply to prevent excess tissue from invaginating between the elongate members 30.

With the expandable member 50 and elongate members 30 expanded as shown in FIG. 2C, external imaging may be utilized, such as ultrasound, CT, fluoroscopy, and the like, e.g., to facilitate dose planning. For example, before treating the patient with radiation therapy, it is generally desirable or necessary to create a dose plan to determine the course of treatment. Dose planning may be accomplished using a variety of imaging methods (e.g., CT or ultrasound) and/or using dose planning software for either HDR or LDR applications. The timing and general scenario of the dose planning process is at the discretion of the clinical physicist/oncologist. For example, with the aid of imaging, both the target tissue region and the position of the elongate members 30 may be delineated. A dose plan may then be developed and, if desired, modified as configuration adjustments are made to the apparatus 10 and/or the elongate members 30. The elongate members 30, core member 20, expandable member 50, and/or other components of the apparatus 10 may include markers (not shown) to facilitate identifying the orientation of the apparatus 10 during dose planning, as described in the applications incorporated by reference elsewhere herein.

Turning to FIG. 2D, after imaging and/or dose planning, the expandable member 50 may be collapsed, e.g., by coupling a syringe or other source of vacuum (not shown) to the fitting 58 and evacuating the inflation media from the interior of the expandable member 50. Alternatively, the expandable member 50 may remain expanded, if desired, e.g., to substantially maintain the surrounding tissue in a defined position relative to the elongate members 30 and/or core member 20. Optionally, the actuator member 62 may be removed to prevent undesired collapse or other movement of the elongate members 30 from the expanded configuration.

One or more sources of radiation (not shown) may be then directed into the elongate members 30 and/or core member 20, e.g., via the openings 36a and tubular extensions 36, and/or into the opening 22a in the proximal end 22 of the core member 20. For example, the elongate members 30 and/or core member 20 may be sized and/or otherwise configured to receive commercially available HDR afterloader transfer tubes (not shown), such as those available from Varian and Nucletron. In an exemplary procedure, an HDR source may be introduced into a first elongate member 30, advanced to a first position, and maintained at the first position for a predetermined time. The HDR source may then be advanced and/or retracted to a second position, and maintained there for a predetermined time, etc. The HDR source may then be removed from the first elongate member 30, and then introduced into the other elongate member 30 (or sequentially into each elongate member if the apparatus 10 includes more than two elongate members, not shown), in a similar manner.

Alternatively, a plurality of LDR sources may be delivered into the elongate members 30 and/or central catheter 20b, and remain indwelling for a predetermined time. For example, individual pods or other radiation sources may be loaded into respective elongate members 30 and/or the core member 20 simultaneously or sequentially, thereby providing a three dimensional array of seeds or radiation sources that may remain in the target location for an extended period of time. The seeds may be spaced apart on each pod and/or may have different radioactive intensities, according to the dose plan.

In a further alternative, one or more radiation sources may be preloaded or secured within the elongate members 30 and/or core member 20 before introduction into the cavity. Thus, radiation may be delivered via the elongate members 30 and/or core member 20 according to a desired treatment plan, as described in the applications incorporated by reference elsewhere herein.

If desired, before, during, or after fractions or treatment(s), one or more instruments may be introduced into the cavity 92 via the working channel member 70. For example, it may be desirable to aspirate fluid or other material that may accumulate within the cavity 92, before each fraction or treatment in a series of treatments. As shown in FIG. 2D, an aspiration catheter 80 may be provided that includes an elongate tubular catheter body 82 including a proximal end 84, a distal end 86 sized for introduction into the working channel member 70, and a lumen (not shown) extending therebetween. The proximal end 84 may be coupled to a syringe or other source of vacuum 80, and the distal end 86 may include one or more openings 88 communicating with the syringe 80 via the aspiration catheter lumen. In addition or alternatively, the aspiration catheter 80 or another instrument may be provided for delivering material into the cavity 92, e.g., before, during, or after treatment(s).

As shown in FIG. 2E, the distal end 86 of the aspiration catheter 80 may be introduced through the fitting 73 and working channel member 70 until the distal end 86 is advanced from the opening 75 and positioned within the cavity 92 adjacent the core member 20 and/or elongate members 30. The syringe 80 (or different syringes, not shown) may be actuated to deliver material into the cavity 92 and/or aspirate material from within the cavity 92. The aspiration catheter 80 may remain stationary during aspiration or may be manipulated to move the distal end 86 within the cavity 92 to facilitate aspiration or material therein. Once sufficient aspiration (or other treatment) is completed, the aspiration catheter 80 may be removed from the working channel member 70. As described above, the working channel member 70 may include a valve, e.g., within the fitting 73, that may seal the working channel after the aspiration catheter 80 is removed. Radiation sources may then be delivered to the target treatment region, as described above.

Optionally, if the course of treatment involves multiple individual treatment sessions, the apparatus 10 may be secured relative to the target tissue region to prevent subsequent migration. For example, tape, an external collar, and/or other features (not shown) may be used to secure the proximal portion 12 of the apparatus 10 extending from the breast 90, e.g., to the patient's skin. Alternatively, the elongate members 30 may sufficiently engage the tissue surrounding the cavity 92 in the expanded configuration to prevent substantial migration. If the apparatus 10 is to remain within the target tissue region for an extended period of time, the tubular extensions 36 and/or the proximal end 22 of the core member 20 may be folded or otherwise directed against the patient's skin where they exit the tract 94, e.g., between treatments, and taped or otherwise secured against the patient's skin. Alternatively, at least a portion of the proximal portion 12 of the apparatus 10, e.g., at least the actuator member 62, may be removable (not shown), e.g., to reduce the profile of the proximal portion 12 extending from the patient's body, as described in the applications incorporated by reference elsewhere herein.

Upon completion of brachytherapy treatment, the actuator member 62 may be reconnected to the apparatus 10 (if removed), and rotated to return the elongate members 30 back to the collapsed configuration. If the expandable member 50 remained expanded during treatment, the expandable member 50 may also be collapsed, e.g., before the elongate members 30, by coupling the syringe 59 or other source of vacuum to the fitting 58 and evacuating the fluid from within the expandable member 50. The apparatus 10 may then be removed from the breast 90 via the tract 94.

Turning to FIGS. 3A-3D, yet another exemplary embodiment of an expandable brachytherapy apparatus 110 is shown that includes a proximal or tail portion 112 and a distal or therapy delivery portion 114, generally defining a longitudinal axis 116 extending therebetween. Similar to the previous embodiment, the apparatus 110 includes an elongate core member 120 including proximal and distal ends 122, 124, a plurality of elongate members 130, a distal hub 126 coupled to the distal end 124, and a proximal hub 160 movable relative to the core member 120. A plurality of tubular extensions 136 may be coupled to the elongate members 130, and an actuator member 162 may be coupled to the core member 120 and/or proximal hub 160, similar to the previous embodiment. Optionally, the apparatus 110 may include a balloon or other expandable member 150 on the distal portion 114, similar to the previous embodiment.

Unlike the previous embodiments, one or more of the elongate members 130 may include an aspiration catheter or member for aspirating material from within a cavity 92, e.g., instead of the working channel member 70 and aspiration catheter 80 described above. For example, all of the elongate members 130 may include a proximal end 132 coupled to the proximal hub 160, a distal end 134 coupled to the distal hub 126, and a lumen (not shown) extending therebetween, similar to the previous embodiment.

However, at least one of the elongate members 130a may include aspiration features as well as providing a pathway for receiving a source of radiation. For example, as best seen in FIG. 3D, one of the elongate members 130a may be an aspiration catheter or other elongate tubular body 180 that includes multiple lumens 182 extending therethrough to provide both a source lumen and aspiration. For example, the aspiration catheter 180 may include one or more aspiration lumens 182s and a central source lumen 182b extending therethrough, e.g., from a proximal housing 188 on the proximal portion 112 to the distal portion 114, possible to the distal hub 126. As shown, the source lumen 182b may be a central, e.g., circular cross-section, lumen and the aspiration lumen(s) 182a may include multiple lumens within the wall of the aspiration catheter 180 at least partially surrounding or otherwise adjacent the source lumen 182b. Alternatively, if desired side-by-side lumens or other configurations may be provided rather than concentric lumens, as shown.

The aspiration catheter 180 may have a substantially uniform construction between the proximal and distal hubs 160, 126 and, optionally, extending to the housing 188 on the proximal portion. For example, the aspiration catheter 180 may be formed as a substantially continuous extrusion or molded tubular body, as desired during manufacturing. Alternatively, the construction of the aspiration catheter 180 may vary between the proximal and distal portions 112, 114 of the apparatus 110, e.g., to provide desired flexibility and/or rigidity.

One or more ports 184 may be provided on the aspiration catheter 180a between the proximal and distal hubs 160, 126, e.g., to allow delivery of material into a cavity or other region adjacent the elongate members 130 and/or aspiration of material from the cavity. For example, a plurality of ports 184 may be provided that are spaced apart from one another between the proximal and distal hubs 160, 126.

As shown in FIGS. 3A and 3B, the housing 188 on the aspiration catheter 180 may have a bifurcated shape, e.g., a "Y" or "T" shape to separate the aspiration lumen(s) 182a and the source lumen 182b. For example, the housing 188 may include a fitting 189, similar to fitting 73, for coupling a syringe 89 or other source of material and/or vacuum to the housing 189, e.g., as shown in FIG. 4D. The fitting 189 may communicate with the aspiration lumen(s) 182a and, optionally, include a valve (not shown), e.g., a Luer valve, for providing a substantially fluid tight seal when the syringe 89 is not coupled to the fitting 189. A tubular extension including an opening 136a may extend from the housing 188 that communicates with the source lumen 182b, e.g., for receiving a source of radiation similar to the tubular extensions 136.

Optionally, the elongate member 130a may include a support member 140 extending at least partially along a length of the aspiration catheter 180, e.g., between the proximal and distal hubs 160, 136, similar to the previous embodiment. For example, the support member 140 may be coupled to the aspiration catheter 180 by one or more sections of heat shrink tubing 186 and the like, similar to the previous embodiment and embodiments in the applications incorporated by reference elsewhere herein.

Turning to FIGS. 5A-5D, in an alternative embodiment generally similar to the apparatus 110, an apparatus 210 may be provided that includes an aspiration member 130a including an aspiration catheter 280a separate from a source lumen catheter 280b. For example, as best seen in FIG. 5D, the aspiration catheter 280a may include an aspiration lumen 282a and the source lumen catheter 280b may include a source lumen 282b. The aspiration and source lumen catheters 280a, 280b may be formed separately, e.g., by extrusion, molding, and the like, and secured together, e.g., by one or more sections of heat shrink tubing 286 and the like. Optionally, a support member 244 may also be secured to the aspiration and source lumen catheters 280a, 280b, e.g., between the proximal and distal hubs 260, 226, by the heat shrink tubing 286. In an alternative embodiment, the aspiration and source lumen catheters 280a, 280b may be attached together, e.g., by bonding with adhesive, fusing, sonic welding, and the like, or may be formed together, e.g., as a co-extrusion and the like.

Turning to FIGS. 4A-4D, the apparatus 110 of FIGS. 3A-3D may be used for brachytherapy treatment within a tissue structure, for example, within a breast 90 (the apparatus 210 of FIGS. 5A-5D may be used in a similar manner for brachytherapy treatment within a tissue structure, for example, within a breast 90, as shown in FIGS. 6A-6D).

Figure 4A:
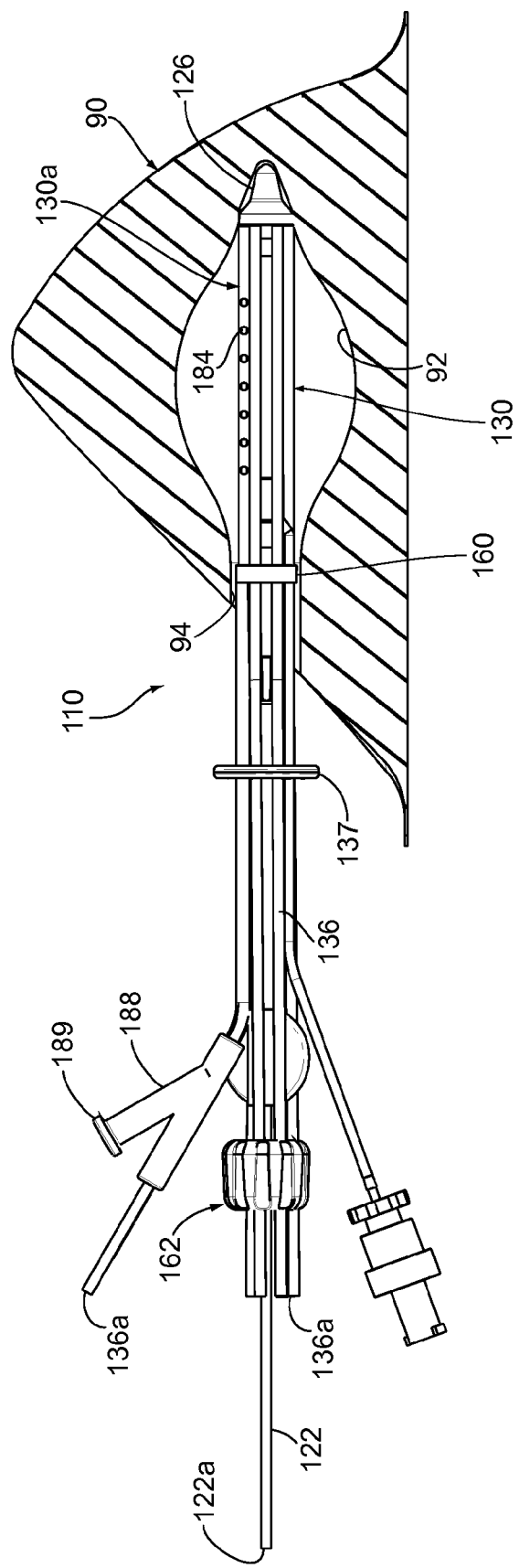
FIGS. 4A-4D are cross-sectional views of a breast, showing a method for treating tissue surrounding a lumpectomy cavity in the breast using the apparatus of FIGS. 3A-3D.

With particular reference to FIG. 4A, the apparatus 110 may be provided initially with the proximal hub 160 and actuator member 162 in a proximal or first position, thereby providing the elongate members 130 in the collapsed condition. The apparatus 110 may be inserted through the tract 94, e.g., through an introducer sheath (not shown), with the elongate members 130 in the collapsed configuration, e.g., until the distal hub 126 is disposed within the cavity 192.

During insertion, the apparatus 110 may be positioned such that the distal hub 126 is placed in the far end of the cavity 92, as shown in FIG. 4A, e.g., such that the elongate members 130 (in the collapsed configuration) extend across and/or partially from the cavity 92, e.g., into the tract 94. Once the apparatus 110 is positioned within the cavity 92, the introducer sheath (if used) may be removed from around the apparatus 110. Thus, as shown in FIG. 4A, with any introducer sheath (or other introducer device) completely removed, the distal portion 114 of the apparatus 110 is positioned within the cavity 92, with the proximal portion 112 extending from the cavity 92, through the tract 94, and/or otherwise out of the breast 90.

Figure 4B:
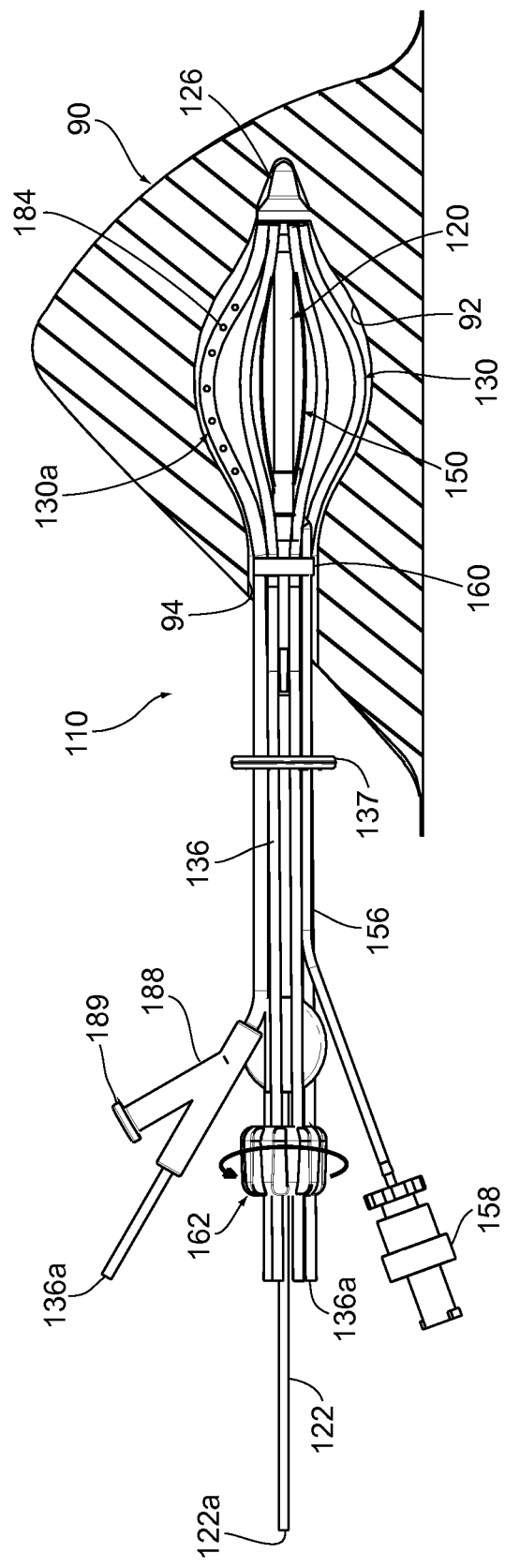

Turning to FIG. 4B, the actuator member 162 may be manipulated to direct the proximal hub 160 distally relative to the distal hub 126, thereby causing the elongate members 130 (including the elongate member 130a including the aspiration catheter 180) to expand outwardly within the cavity 92. For example, the actuator member 162 may be rotated in a first direction to expand the elongate members 130 to the expanded configuration. When the apparatus 110 is directed to the expanded configuration, the elongate members 130 may have sufficient bias to at least partially direct tissue surrounding the cavity outwardly and/or cause the tissue to invaginate between adjacent elongate members 130, similar to the methods described elsewhere herein.

Figure 4C:
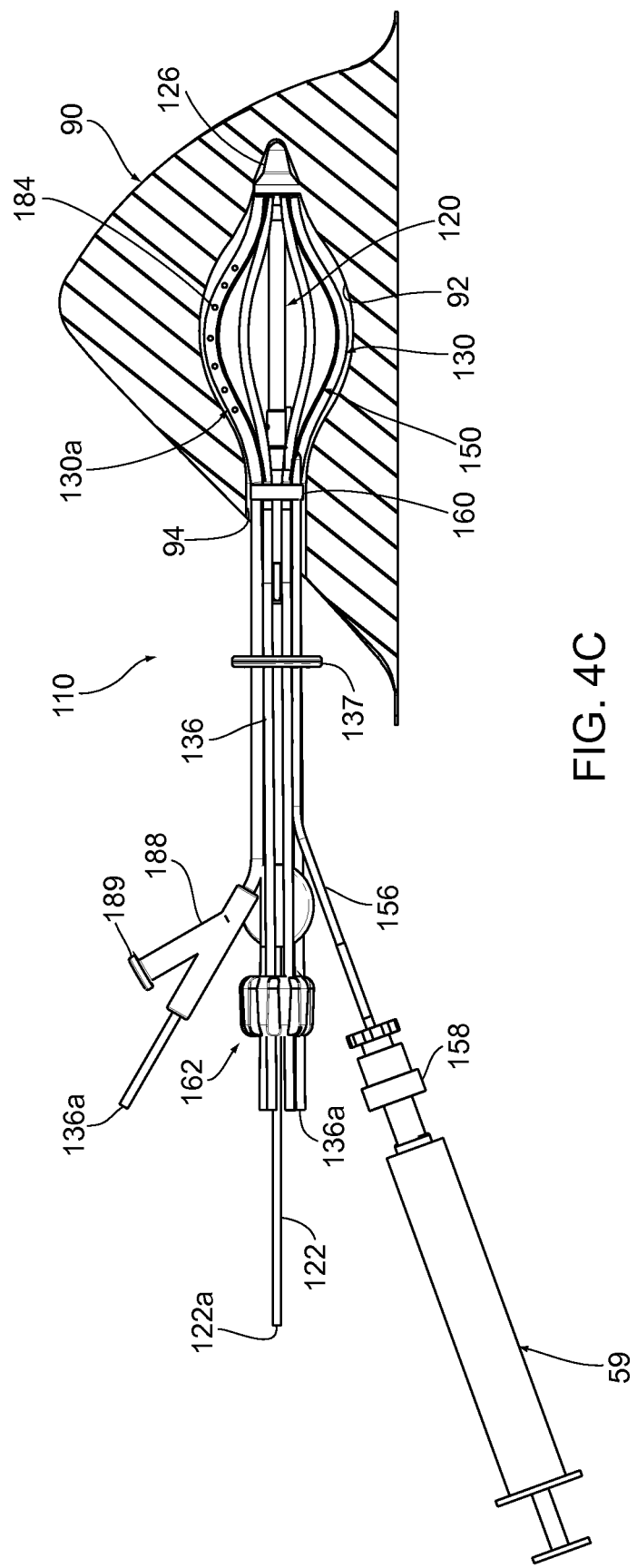
Figure 4D:
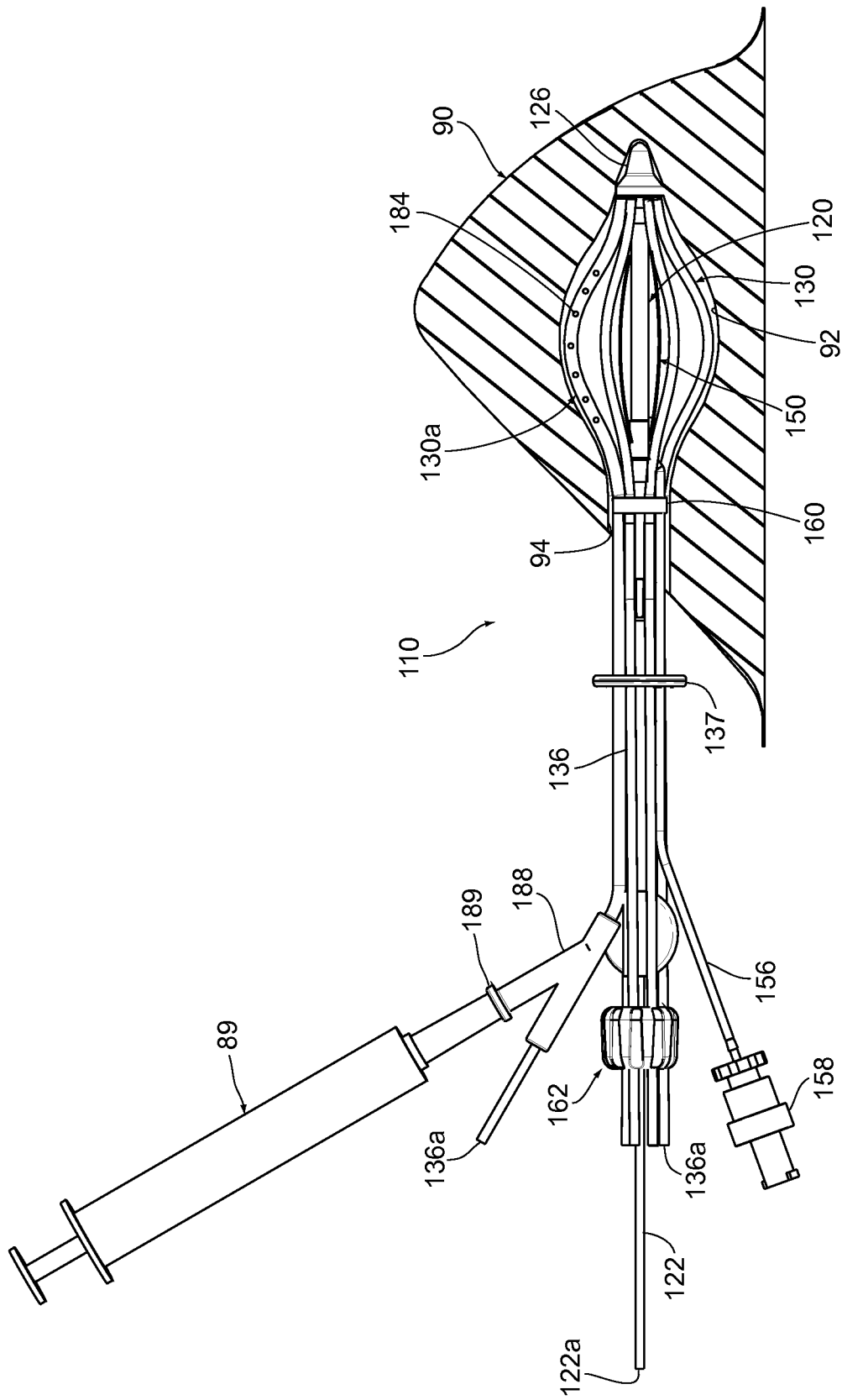
Figure 6A:
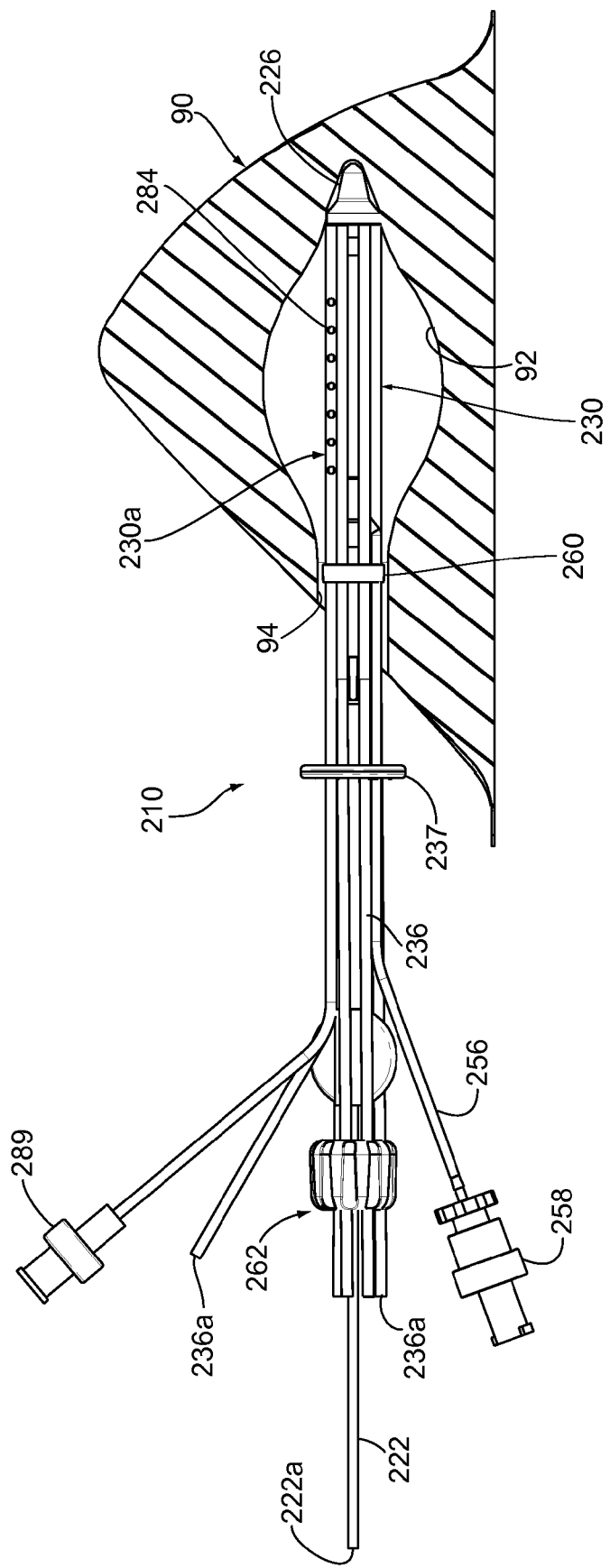
FIGS. 6A-6D are cross-sectional views of a breast, showing a method for treating tissue surrounding a lumpectomy cavity in the breast using the apparatus of FIGS. 5A-5D.
Figure 6B:
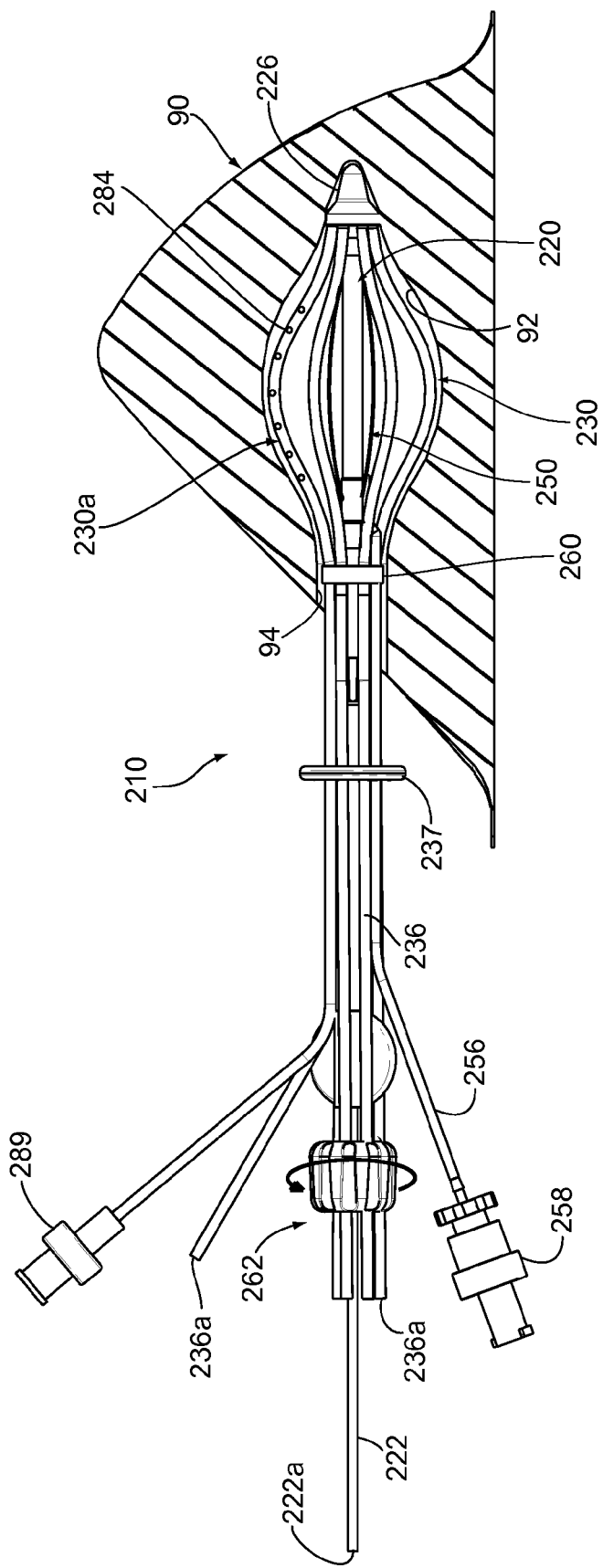
Figure 6C:
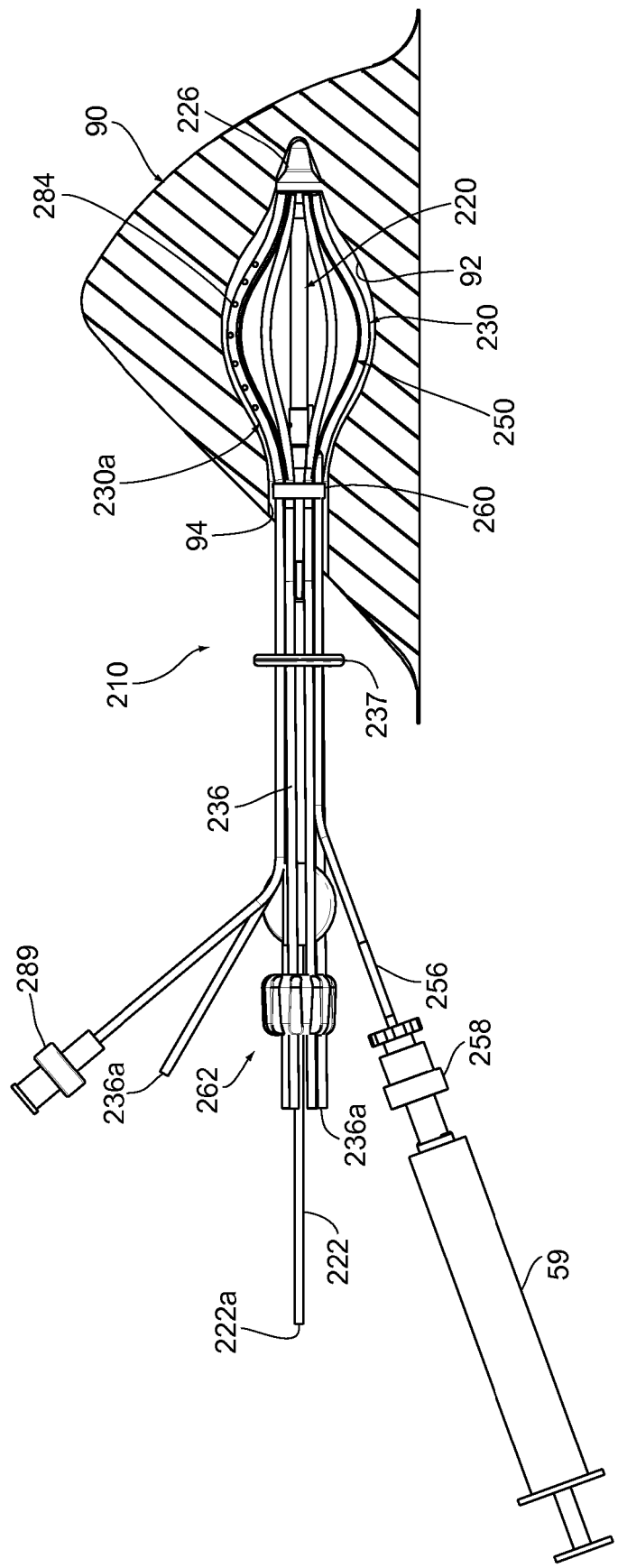
Figure 6D:
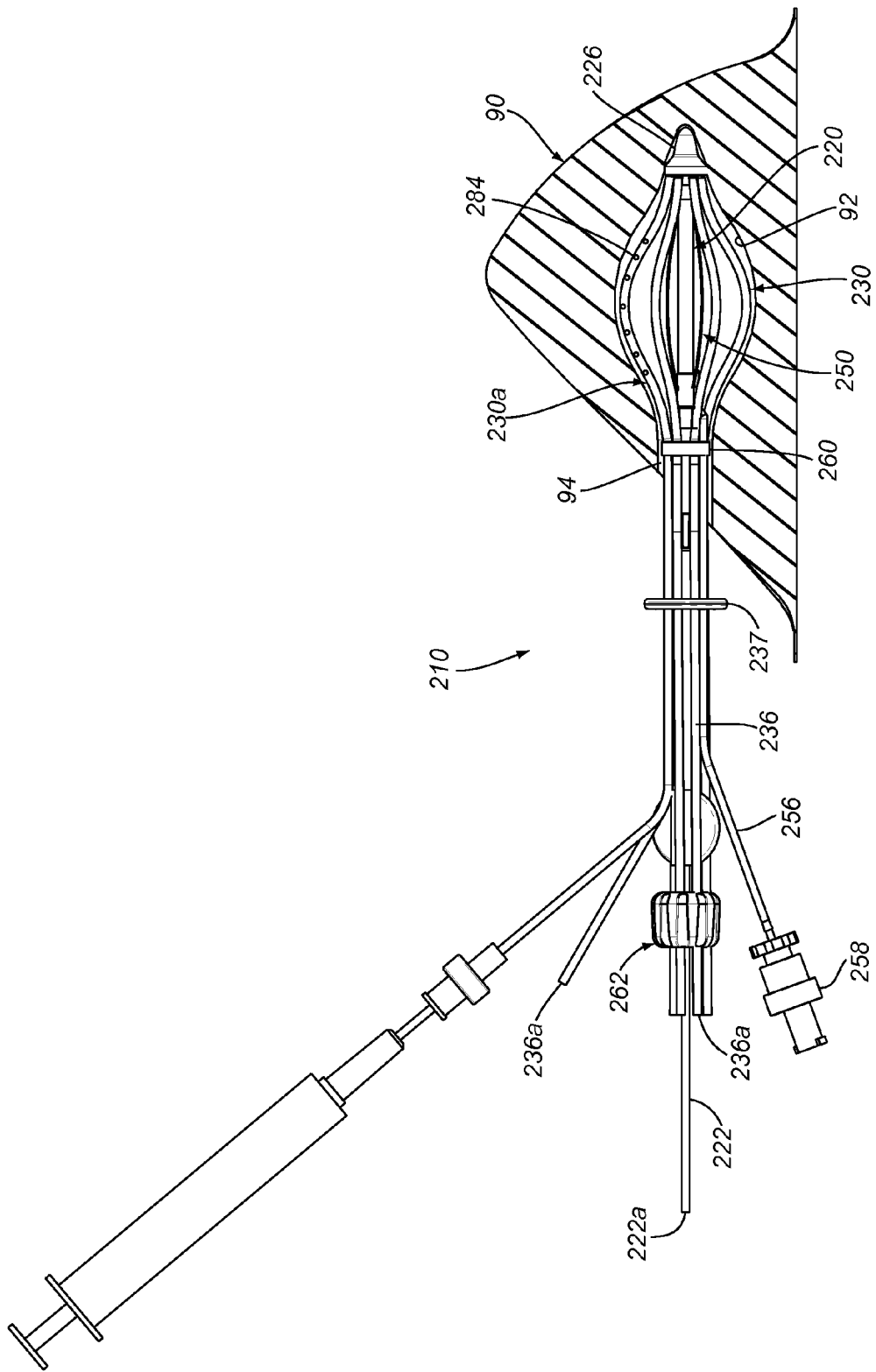

Turning to FIG. 4C, once the elongate members 130 are directed to the expanded configuration, the expandable member 150 may be expanded, e.g., by coupling a syringe or other source of inflation media 59 to the fitting 158 and introducing inflation media into the interior of the expandable member 150. Similar to the other embodiments herein, the inflation media may be compatible and/or enhance external imaging of the apparatus 110, cavity 92, and/or surrounding tissue.

The expandable member 150 may be expanded until the expandable member 150 presses against or otherwise contacts the elongate members 130 and/or surrounding tissue. For example, the expandable member 150 may be expanded sufficiently to further shape the cavity 92 and/or surrounding tissue in addition to any shaping achieved with the elongate members 130 alone, and/or to substantially fill any voids or gaps within the cavity 92. Alternatively, the expandable member 150 may be expanded until it is spaced slightly away from the elongate members 130, e.g., simply to prevent excess tissue from invaginating between the elongate members 130.

With the expandable member 150 and elongate members 130 expanded as shown in FIG. 4C, external imaging may be utilized, such as ultrasound, CT, fluoroscopy, and the like, e.g., to facilitate dose planning. For example, with the aid of imaging, both the target tissue region and the position of the elongate members 130 may be delineated. A dose plan may then be developed and, if desired, modified as configuration adjustments are made to the apparatus 110 and/or the elongate members 130. Optionally, the elongate members 130, core member 120, expandable member 150, and/or other components of the apparatus 110 may include markers (not shown) to facilitate identifying the orientation of the apparatus 110 during dose planning, as described elsewhere herein.

Turning to FIG. 4D, after imaging and/or dose planning, the expandable member 150 may be collapsed, e.g., by coupling a syringe or other source of vacuum (not shown) to the fitting 158 and evacuating the inflation media from the interior of the expandable member 150. Alternatively, the expandable member 150 may remain expanded, if desired, e.g., to substantially maintain the surrounding tissue in a defined position relative to the elongate members 130 and/or core member 120. Optionally, the actuator member 162 may be removed to prevent undesired collapse or other movement of the elongate members 130 from the expanded configuration.

One or more sources of radiation (not shown) may be then directed into the elongate members 130 and/or core member 120, e.g., via the openings 136a and tubular extensions 136, and/or into the opening 122a in the proximal end 122 of the core member 120, similar to other embodiments herein.

Optionally, if the course of treatment involves multiple individual treatment sessions, the apparatus 110 may be secured relative to the cavity 92 and/or breast 90, e.g. to prevent subsequent migration. Alternatively, the elongate members 130 may sufficiently engage the tissue surrounding the cavity 92 in the expanded configuration to prevent substantial migration. If the apparatus 110 is to remain within the target tissue region for an extended period of time, the tubular extensions 136 and/or the proximal end 122 of the core member 120 may be folded or otherwise directed against the patient's skin where they exit the tract 94, e.g., between treatments, and taped or otherwise secured against the patient's skin. Alternatively, at least a portion of the proximal portion 112 of the apparatus 110, e.g., at least the actuator member 162, may be removable (not shown), e.g., to reduce the profile of the proximal portion 112 extending from the patient's body, as described elsewhere herein.

Upon completion of brachytherapy treatment, the actuator member 162 may be reconnected to the apparatus 110 (if removed), and rotated, e.g., in a second opposite direction, to return the elongate members 130 back to the collapsed configuration. If the expandable member 150 remained expanded during treatment, the expandable member 150 may also be collapsed, e.g., before the elongate members 130, by coupling the syringe 59 or other source of vacuum to the fitting 158 and evacuating the fluid from within the expandable member 150. The apparatus 110 may then be removed from the breast 90 via the tract 94.

The apparatus described herein may permit brachytherapy devices (or other radiation sources), via a single point of entry, to deliver radiation to the tissue surrounding a cavity from a position within the cavity. Moreover, the intracavitary apparatus, methods, and systems described herein may permit substantial fixation of one or more radiation sources relative to the target tissue region surrounding the cavity. The surrounding tissue may invaginate sufficiently around the devices to ensure adequate fixation and/or sufficient depth of penetration of the desired radiation dose to the tissue adjacent the lumpectomy cavity throughout the implantation period. As a result, the desired dose delivery to specific tissue may be achieved over the course of brachytherapy treatment. Moreover, irradiation of unintended tissue, e.g., due to movement of the device relative to the surrounding tissue, may be minimized.

The brachytherapy devices described herein may be implanted into (and/or around) a tumor before surgical excision (neoadjuvantly), and then subsequently removed before or at the time of surgery. Such treatments may shrink or even destroy the tumor. In other embodiments, the apparatus and methods described herein may be used to deliver brachytherapy after surgically removing tumor tissue to treat surrounding tissue post-operatively (post-lumpectomy in breast). In some instances, it is contemplated that brachytherapy apparatus and methods described and illustrated herein may supplement or reduce the need for conventional treatment options, e.g., tumor excision, full field external beam radiation therapy (EBRT), and chemotherapy. Alternatively, the methods described herein may be performed adjuvantly with these and other treatments, e.g., with chemotherapy, EBRT.

Treatment in accordance with the present invention may also avoid some of the disadvantages of HDR treatment, e.g., high activity, exposure of unintended tissue, potentially bulky and protruding catheters, and/or the need for numerous patient visits to receive treatment. Alternatively, the apparatus and methods described herein may be used to perform HDR treatment, e.g., by delivering one or more HDR radiation sources along pathways of the devices in accordance with known HDR dose plans. In a further alternative, a HDR radiation source (e.g., an Iridium tipped afterloader cable from Varian Medical Systems, Inc., or a small diameter x-ray source, such as those disclosed in U.S. Publication No. 2005/0061533A1, the disclosure of which is expressly incorporated by reference herein) may be advanced through any of the core members described herein, with the expandable devices opening a cavity to facilitate delivering radiation more evenly to the tissue surrounding the cavity. Optionally, the core member may shield the radiation source to direct radiation from the radiation source towards a desired portion of the surrounding tissue.

The brachytherapy devices described herein are also substantially flexible, in comparison to conventional HDR catheters, such that they may be placed in either a straight or curvilinear (e.g., curved or spiral) fashion. Such flexibility may permit implantation of radiation sources (e.g., seeds) in configurations and locations that otherwise may be considered inaccessible.

Apparatus and methods of the present invention may also potentially achieve desired dosage with relatively few catheters. For example, the apparatus and methods described herein potentially may obtain desired dose delivery levels with fewer catheters per target than is typically utilized with conventional HDR methods. Yet, the devices described herein may still be implanted with the use of conventional imaging methods (e.g. stereotactic X-ray, ultrasound, CT).

Apparatus and methods of the present invention may also provide other benefits to the patient. For example, potentially less skin damage and discomfort may result from smaller and more flexible catheter insertions. Further, the small flexible tail portions, once in their proper position, may be trimmed short, but may also be folded and taped against the skin, unlike rigid HDR catheters. Thus, the patient may have less discomfort over the course of treatment and potentially improved post-procedural cosmesis. Further, for example, apparatus and techniques in accordance with the present invention may potentially result in reduced side effects as compared to other treatments, e.g., EBRT and chemo, and may require fewer hospital visits over the course of the treatment regimen as compared to, for example, current HDR brachytherapy.

Still further, the brachytherapy delivery systems described herein may provide a standardized dose of radiation based upon lesion size. As a result, the need for extensive dose calculating and mapping systems may potentially be reduced or eliminated with certain cancers (e.g., breast).

The complete disclosure of the patents, patent documents, and publications cited in the Background, the Detailed Description of Exemplary Embodiments, and elsewhere herein are incorporated by reference in their entirety as if each were individually incorporated. Additional information on brachytherapy apparatus that include features that may be incorporated into the embodiments described herein and on methods for using such apparatus may be found in co-pending application Ser. No. 10/658,518, filed Sep. 9, 2003, now U.S. Pat. No. 7,601,113, Ser. No. 11/276,851, filed Mar. 16, 2006, published as U.S. Publication No. 2007/0106108, 60/803,828, filed Jun. 2, 2006, Ser. No. 11/757,231, filed Jun. 1, 2007, published as U.S. Publication No. 2008/0221384, Ser. No. 11/868,483, filed Oct. 6, 2007, published as U.S. Publication No. 2008/0091055, and Ser. No. 12/543,469, filed Aug. 18, 2009, published as U.S. Publication No. 2010/0048967. The entire disclosures of these applications are expressly incorporated by reference herein.

Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. For example, any of the treatment devices described herein may be combined with any of the delivery systems and methods also described herein. Thus, the invention is limited only by the following claims, and equivalents thereto.

We claim:

1. A brachytherapy treatment apparatus, comprising:
an elongate core member comprising proximal and distal ends, a proximal portion, and a distal portion configured for introduction into a tract through tissue and terminating in a distal tip;
a plurality of elongate members, each elongate member comprising a distal end coupled to the core member distal end, a proximal end movable relative to the core member, and a pathway extending between the elongate member proximal and distal ends for receiving a source of radiation therealong, the elongate member proximal ends being movable relative to the distal ends for expanding the elongate members from a collapsed configuration to an expanded configuration such that the elongate members are directed radially outwardly away from the distal portion of the core member;
an expandable member comprising a proximal end coupled to the core member adjacent the elongate member proximal ends and a distal end coupled to the distal tip of the core member such that the expandable member surrounds the distal portion of the core member, the elongate members extending along and unsecured to an outer surface of the expandable member in the collapsed configuration; and
an actuator hub coupled to the elongate members and an elongate actuator member extending proximally from the hub that is movable axially relative to the core member for expanding the elongate members independently of the expandable member such that the elongate members are expanded away from the expandable member only by actuating the actuator member independently of the expandable member while the expandable member remains in an unexpanded condition.

2. The apparatus of claim 1, further comprising an inflation lumen extending distally from the proximal portion and communicating with an interior of the expandable member for delivering inflation media into the interior for expanding the expandable member.

3. The apparatus of claim 1, wherein each elongate member comprises a tubular member and an elongate support for biasing the tubular member to maintain a predetermined arcuate shape when the elongate member is directed from the collapsed configuration to the expanded configuration.

4. The apparatus of claim 1, wherein the core member comprises a pathway for receiving a source of radiation.

5. The apparatus of claim 1, further comprising a source of radiation introduceable along the pathways for delivering radiation to the target location.

6. The apparatus of claim 1, further comprising a working channel member extending from the proximal end of the core member to the distal portion of the core member, the working channel member comprising a lumen extending from the core member proximal end to an opening adjacent the distal portion and exposed to the outer surface of the expandable member.

7. The apparatus of claim 6, further comprising an aspiration catheter including a proximal end, a distal end sized for introduction through the working channel, and a lumen extending therebetween, the aspiration catheter proximal end coupled to a vacuum source for aspirating material into the aspiration catheter lumen via an opening in the aspiration catheter distal end.

8. The apparatus of claim 6, wherein the working channel member comprises a valve within the lumen for selectively sealing the lumen.

9. The apparatus of claim 8, wherein the valve is biased closed and is configured to be opened when an instrument is introduced through the lumen of the working channel member.

10. The apparatus of claim 1, wherein one of the elongate members comprises an aspiration member including one or more ports adjacent the distal portion communicating with an aspiration lumen extending to a proximal end of the aspiration member.

11. The apparatus of claim 10, further comprising a vacuum source coupled to the proximal end of the aspiration member for aspirating material into the aspiration lumen via the one or more ports.

12. The apparatus of claim 10, wherein the aspiration member is disposed adjacent a tubular member comprising a source lumen therein providing a pathway for receiving a source of radiation therealong.

13. The apparatus of claim 10, wherein the aspiration member comprises a source lumen therein providing a pathway for receiving a source of radiation therealong.

14. The apparatus of claim 1, wherein the actuator member comprises a tubular body disposed around a portion of the core member, the tubular body rotatable relative to the core member to cause the hub to move axially relative to the core member and direct the elongate members to the expanded configuration.

15. A brachytherapy treatment apparatus, comprising:
an elongate core member comprising proximal and distal ends, a proximal portion, and a distal portion configured for introduction into a tract through tissue and terminating in a distal tip;
a distal hub coupled to the distal tip of the core member;
a proximal hub movably mounted on the core member proximal to the distal hub;
a plurality of elongate catheters comprising distal ends coupled to the distal hub, proximal ends coupled to the proximal hub, elongate portions that extend between the proximal and distal hubs, and lumens extending between the respective catheter proximal and distal ends for receiving a source of radiation therealong;
an elongate actuator member coupled to and extending proximally from the proximal hub, the actuator member being actuatable for moving the catheters from a collapsed configuration to an expanded configuration such that the elongate portions are directed radially outwardly away from the core member;
an expandable member comprising a proximal end coupled to the proximal hub and a distal end coupled to the distal hub such that the expandable member surrounds the distal portion of the core member, the catheters extending along and unsecured to an outer surface of the expandable member in the collapsed configuration; and
a working channel member extending between the proximal and distal portions of the core member, the working channel member comprising a proximal end and a distal end disposed between the proximal and distal ends of the expandable member, and a lumen extending therebetween such that an opening in the working channel distal end communicating with the working channel lumen is located outside the outer surface of the expandable member between the proximal and distal ends of the expandable member.

16. The apparatus of claim 15, wherein the actuator member is movable axially relative to the core member to expand the catheters independently of the expandable member such that the catheters may be expanded away from the expandable member before the expandable member is expanded.

17. The apparatus of claim 16, further comprising an inflation lumen extending distally from the proximal portion and communicating with an interior of the expandable member for delivering inflation media into the interior for expanding the expandable member.

18. The apparatus of claim 15, further comprising an aspiration catheter including a proximal end, a distal end sized for introduction through the working channel lumen, and a lumen extending therebetween, the aspiration catheter proximal end coupled to a vacuum source for aspirating material into the aspiration catheter lumen via an opening in the aspiration catheter distal end.

19. The apparatus of claim 15, wherein the working channel member comprises a valve within the working channel lumen for selectively sealing the working channel lumen.

20. A brachytherapy treatment apparatus, comprising:
an elongate core member comprising proximal and distal ends, a proximal portion, and a distal portion configured for introduction into a tract through tissue and terminating in a distal tip;
a distal hub coupled to the distal tip of the core member;
a proximal hub movably mounted on the core member proximal to the distal hub;
a plurality of elongate catheters comprising distal ends coupled to the distal hub, proximal ends coupled to the proximal hub, elongate portions that extend between the proximal and distal hubs, and lumens extending between the respective catheter proximal and distal ends for receiving a source of radiation therealong;
an actuator member coupled to and extending proximally from the proximal hub, the actuator member being actuatable for moving the catheters from a collapsed configuration to an expanded configuration such that the elongate portions are directed radially outwardly away from the core member; and
an expandable member comprising a proximal end coupled to the proximal hub and a distal end coupled to the distal hub such that the expandable member surrounds the distal portion of the core member, the catheters extending along and unsecured to an outer surface of the expandable member in the collapsed configuration,
wherein one of the catheters comprises an aspiration member including one or more ports located outside the outer surface of the expandable member between the proximal and distal ends of the expandable member and communicating with an aspiration lumen extending to a proximal end of the aspiration member.

21. A method for brachytherapy treatment of tissue surrounding a cavity within a target location of a body, comprising:
advancing a distal portion of an elongate body comprising a core member defining a central axis and carrying a plurality of elongate members into the cavity with the elongate members in a collapsed configuration such that an elongate actuator member extends from the distal portion and a proximal end of the actuator member is disposed outside the body;

actuating the proximal end of the actuator member to move an actuator hub on the distal portion axially relative to the core member and direct the elongate members to an expanded configuration within the cavity to position portions of the elongate members away from the central axis and adjacent tissue surrounding the cavity while an expandable member on the distal portion between the core member and the elongate members remains in an unexpanded condition;

expanding the expandable member outwardly towards the expanded elongate members without moving the actuator hub; and delivering radiation to the target location via the elongate members to treat tissue at the target location.

22. The method of claim 21, further comprising:
with the expandable member expanded, imaging at least the distal portion of the elongate body and tissue surrounding the cavity to develop a dose plan; and
collapsing the expandable member after imaging and before delivering radiation to the target location via the elongate members.

23. The method of claim 21, wherein the expandable member remains expanded while radiation is delivered to the target location.

24. The method of claim 21, further comprising:
introducing an aspiration catheter into the cavity outside the expandable member via a working channel on the elongate body; and
aspirating material within the cavity via the aspiration catheter.

25. The method of claim 21, wherein at least one of the elongate members comprises one or more ports on the distal portion, the method further comprising:
aspirating material within the cavity outside the expandable member via the one or more ports.

26. The method of claim 21, wherein the actuator member comprises a tubular body disposed around a portion of the core member, and wherein actuating the proximal end of the actuator member comprises rotating the proximal end of the tubular body to move the actuator axially relative to the core member and direct the elongate members to the expanded configuration.

27. A method for brachytherapy treatment of tissue surrounding a cavity within a target location of a body, comprising:

advancing a distal portion of an elongate body comprising a core member defining a central axis and carrying a plurality of elongate members into the cavity with the elongate members in a collapsed configuration such that an elongate actuator member extends from the distal portion and a proximal end of the actuator member is disposed outside the body;

actuating the proximal end of the actuator member to move an actuator hub on the distal portion axially relative to the core member and direct the elongate members to an expanded configuration within the cavity to position portions of the elongate members away from the central axis and adjacent tissue surrounding the cavity while an expandable member on the distal portion between the core member and the elongate members remains in an unexpanded condition;

expanding the expandable member outwardly towards the expanded elongate members without moving the actuator hub;

imaging at least the distal portion of the elongate body and tissue surrounding the cavity to develop a dose plan;

collapsing the expandable member after imaging while the elongate members remain in the expanded configuration; and delivering radiation to the target location via the expanded elongate members to treat tissue at the target location while the expandable member remains collapsed.

* * * * *